(12) United States Patent
Jeong

(10) Patent No.: US 9,241,727 B2
(45) Date of Patent: Jan. 26, 2016

(54) TOOL FOR MINIMALLY INVASIVE SURGERY AND METHOD FOR USING THE SAME

(76) Inventor: Chang Wook Jeong, Seoul (KR)

( * ) Notice: Subject to any disclaimer, the term of this patent is extended or adjusted under 35 U.S.C. 154(b) by 454 days.

(21) Appl. No.: 13/058,808

(22) PCT Filed: Aug. 12, 2009

(86) PCT No.: PCT/KR2009/004515
§ 371 (c)(1),
(2), (4) Date: Feb. 11, 2011

(87) PCT Pub. No.: WO2010/019001
PCT Pub. Date: Feb. 18, 2010

(65) Prior Publication Data
US 2011/0152922 A1  Jun. 23, 2011

(30) Foreign Application Priority Data

Aug. 12, 2008 (KR) .................. 10-2008-0079126

(51) Int. Cl.
*A61B 17/00* (2006.01)
*A61B 17/29* (2006.01)

(52) U.S. Cl.
CPC ............. *A61B 17/29* (2013.01); *A61B 17/2909* (2013.01); *A61B 2017/00738* (2013.01); *A61B 2017/2901* (2013.01); *A61B 2017/291* (2013.01); *A61B 2017/2906* (2013.01); *A61B 2017/2908* (2013.01); *A61B 2017/2923* (2013.01); *A61B 2017/2927* (2013.01)

(58) Field of Classification Search
CPC .... A61B 17/29; A61B 2017/2901–2017/2908; A61B 17/2909; A61B 2017/291; A61B 2017/2919–2017/2923; A61B 19/2203; A61B 2019/2207–2019/2296; F16C 11/00; F16C 11/04
USPC ............. 606/129–130, 141–142, 205–210, 1; 403/52; 901/28
See application file for complete search history.

(56) References Cited

U.S. PATENT DOCUMENTS

| | | | | |
|---|---|---|---|---|
| 5,395,367 A | * | 3/1995 | Wilk | ................................. 606/1 |
| 5,630,831 A | * | 5/1997 | Lahr | ............................. 606/207 |
| 5,810,716 A | * | 9/1998 | Mukherjee | ............. A61B 19/22 |
| | | | | 600/139 |
| 6,685,698 B2 | | 2/2004 | Morley et al. | |

(Continued)

FOREIGN PATENT DOCUMENTS

| | | |
|---|---|---|
| JP | 2008036219 A | 2/2008 |
| JP | 2008114339 A | 5/2008 |

OTHER PUBLICATIONS

International Search Report for PCT Application PCT/KR2009/004515, Korean Intellectual Property Office, Feb. 23, 2010.

*Primary Examiner* — Katherine Rodjom
*Assistant Examiner* — Jonathan Hollm
(74) *Attorney, Agent, or Firm* — Mayer Brown LLP; Hyunho Park

(57) ABSTRACT

A tool for minimally invasive surgery includes a main shaft, a first control shaft and a second control shaft, a first actuating shaft and a second actuating shaft, an adjustment handle, an end effector, a pitch control part, a first yaw control part and a second yaw control part, a pitch actuating part, a first yaw actuating part and a second yaw actuating part, and a pitch cable, a first yaw cable and a second yaw cable.

12 Claims, 47 Drawing Sheets

(56) References Cited

U.S. PATENT DOCUMENTS

| | | | |
|---|---|---|---|
| 6,743,239 B1 * | 6/2004 | Kuehn | A61B 17/0643 464/149 |
| 7,147,650 B2 * | 12/2006 | Lee | 606/205 |
| 2002/0111621 A1 | 8/2002 | Wallace et al. | |
| 2003/0036748 A1 * | 2/2003 | Cooper et al. | 606/1 |
| 2004/0199147 A1 * | 10/2004 | Nishizawa et al. | 606/1 |
| 2006/0047307 A1 * | 3/2006 | Ortiz et al. | 606/219 |
| 2006/0155262 A1 * | 7/2006 | Kishi et al. | 606/1 |

* cited by examiner

TOOL FOR MINIMALLY INVASIVE SURGERY AND METHOD FOR USING THE SAME

PRIORITY

The present application claims priority under 35 U.S.C. §371 to PCT Application PCT/KR2009/004515, filed on Aug. 12, 2009, which claims priority to Korean Patent Application No. 10-2008-0079126, filed on Aug. 12, 2008, the disclosures of which are hereby incorporated by reference in their entireties.

FIELD OF THE INVENTION

The present invention relates to an easy-to-control tool for minimally invasive surgery and a method for using the same, and more specifically, to a tool for minimally invasive surgery, which performs minimally invasive surgery in a dexterous and convenient manner by actuating an end effector through the control of an adjustment handle, and a method for using the same.

BACKGROUND OF THE INVENTION

Minimally invasive surgery is a surgical approach that involves use of instruments inserted through several tiny incision openings to perform a surgery causing minimal tissue trauma.

This minimally invasive surgery relatively reduces changes in metabolism of the patient in the period of post-surgical care, so it is beneficial to rapid recovery of the patient. Therefore, using such minimally invasive surgery shortens length of a hospital stay of the patient after the surgery and allows patients to return to normal physical activities more quickly. In addition, minimally invasive surgery causes less pain and reduces scar to patients after surgery.

The most general form of the minimally invasive surgery is endoscopy. Among them, a laparoscopy that involves minimally-invasive inspection and operation inside abdominal cavity is known as the most general form of endoscopy. To operate the standard laparoscopic surgery, an abdomen of the patient is insufflated with gas, and small incisions (about ½ inch or less) are formed for use as an entrance of a tool for the laparoscopic surgery, through which a trocar is inserted. In general, laparoscopic surgical tools include a laparoscope (for observation of a surgical site) and other working tools. Here, the working tools are similar in structure to the conventional tools used for small incision surgery, except that the end effector or working end of each tool is separated from its handle by an elongated shaft. For instance, working tools may include a clamp, a grasper, scissors, a stapler, needle holder, and so forth. To perform the surgery, a user, such as a surgeon, puts the working tool into a surgical site through the trocar, and manipulates it from the outside of abdominal cavity. Then, the surgeon monitors the procedure of the surgery through a monitor that displays the image of the surgical site that is taken by the laparoscope. The endoscopic approach similar to this is broadly used in retroperitoneoscopy, pelviscopy, arthroscopy, cisternoscopy, sinuscopy, hysteroscopy, nephroscopy, cystoscopy, urethroscopy, pyeloscopy, and so on.

Although this minimally invasive surgery has a number of advantages, it has shortcomings in the difficulty of approaching the conventional minimally invasive surgical tools to a surgical site and the inconvenient or complicate manipulation of such tools because of an end effector connected to a rigid and long shaft. Particularly, since the traditional end effector has no bending portion like a joint, it is difficult to perform a dexterous handling required for surgery. Moreover, when a surgical site is located behind a specific organ, the conventional minimally invasive surgical tools cannot even approach there.

Also, traditionally, many surgical tools were often used together even for minimally invasive surgery, and because of that many incisions were formed in a patient's body. An attempt to solve such a problem has been made by proposing the idea of forming only one incision and then inserting a trocar into the incision for surgery, but unfortunately there is no suitable tool for supporting the idea.

In view of the foregoing, the present inventor noticed that all the problems mentioned above are, after all, the main impediment to the wide expansion of minimally invasive surgery.

SUMMARY OF THE INVENTION

The present invention is directed to solve all of the problems mentioned above.

Another object of the present invention is to provide a tool for minimally invasive surgery, which has an end effector of high-degree-of-freedom motion.

Still another object of the present invention is to provide a tool for minimally invasive surgery, which operates in a dexterous manner with relatively simple drive control elements.

Still another object of the present invention is to provide a tool for minimally invasive surgery, which easily accesses to areas that are hidden by specific organs, including plural joint portions, for surgery.

Still another object of the present invention is to provide a surgical tool for achieving a minimally invasive surgery in a dexterous and convenient manner with the least number of incisions in a patient's body, most preferably, with only one incision.

Still another object of the present invention is to provide a tool for minimally invasive surgery, which is more technically advanced than the minimally invasive surgical tools that are disclosed in Korean Patent Application Nos. 2008-51248 and 2008-61894 filed by the same inventor.

Yet another object of the present invention is to provide a novel method for using a tool for minimally invasive surgery in accordance with the present invention.

In accordance with an aspect of the present invention, there is provided a tool for minimally invasive surgery comprising a main shaft, a first control shaft and a second control shaft positioned in sequence from one end of the main shaft, a first actuating shaft and a second actuating shaft positioned in sequence from the other end of the main shaft, an adjustment handle positioned around one end of the second control shaft, an end effector positioned around one end of the second actuating shaft, a pitch control part positioned around one position of the positions between the main shaft and the first control shaft, between the first control shaft and the second control shaft, and between the second control shaft and the adjustment handle, for transferring a motion of the adjustment handle in a pitch direction to the end effector, a first yaw control part and a second yaw control part positioned around the other positions of the positions between the main shaft and the first control shaft, between the first control shaft and the second control shaft, and between the second control shaft and the adjustment handle, respectively, for transferring a motion of the adjustment handle in a yaw direction to the end effector, a pitch actuating part positioned around one position of the positions between the main shaft and the first actuating shaft, between the first actuating shaft and the second actuating shaft, and between the second actuating shaft and the end effector, a first yaw actuating part and a second yaw actuating part positioned around the other positions of the positions between the main shaft and the first actuating shaft, between the first actuating shaft and the second actuating shaft, and between the second actuating shaft and the end effector, respectively, and a pitch cable, a first yaw cable, and a second yaw cable for transferring motions from the pitch control part, the first yaw control part, and the second yaw control part to the pitch actuating part, the first yaw actuating part, and the second yaw actuating part.

In accordance with another aspect of the present invention, there is provided a tool for minimally invasive surgery comprising, a main shaft, a first control shaft and a second control shaft positioned in sequence from one end of the main shaft, a first actuating shaft and a second actuating shaft positioned in sequence from the other end of the main shaft, an adjustment handle positioned around one end of the second control shaft, an end effector positioned around one end of the second actuating shaft, a pitch control part positioned between the second control shaft and the adjustment handle for transferring a motion of the adjustment handle in a pitch direction to the end effector, a first yaw control part positioned between the main shaft and the first control shaft for transferring a motion of the adjustment handle in a yaw direction to the end effector, a second yaw control part positioned between the first control shaft and the second control shaft for transferring a motion of the adjustment handle in a yaw direction to the end effector, a third yaw control part positioned near the pitch control part for transferring a motion of the adjustment handle in a yaw direction to the end effector, a pitch actuating part positioned between the second actuating shaft and the end effector, a first yaw actuating part positioned between the main shaft and the first actuating shaft, a second yaw actuating part positioned between the first actuating shaft and the second actuating shaft, a third yaw actuating part positioned near the pitch actuating part, and a pitch cable, a first yaw cable, a second yaw cable, and a third yaw cable for transferring motions from the pitch control part, the first yaw control part, the second yaw control part, and the third yaw control part to the pitch actuating part, the first yaw actuating part, the second yaw actuating part, and the third yaw actuating part.

In accordance with yet another aspect of the present invention, there is provided a tool for minimally invasive surgery comprising, a main shaft, a first actuating shaft and a second actuating shaft positioned in sequence from one end of the main shaft, a controller positioned around the other end of the main shaft, an end effector positioned around one end of the second actuating shaft, a pitch actuating part positioned around one position of the positions between the main shaft and the first actuating shaft, between the first actuating shaft and the second actuating shaft, and between the second actuating shaft and the end effector, a first yaw actuating part and a second yaw actuating part positioned around the other positions of the positions between the main shaft and the first actuating shaft, between the first actuating shaft and the second actuating shaft, and between the second actuating shaft and the end effector, respectively, and a pitch cable, a first yaw cable, and a second yaw cable for controlling the pitch actuating part, the first yaw actuating part, and the second yaw actuating part, wherein the controller comprises a pitch control module for controlling the pitch actuating part, a first yaw control module for controlling the first yaw actuating part, and a second control module for controlling the second yaw actuating part.

BRIEF DESCRIPTION OF THE DRAWINGS

The above and other objects and features of the present invention will become apparent from the following description of the preferred embodiments given in conjunction with the accompanying drawings, in which.

DETAILED DESCRIPTION OF THE PREFERRED EMBODIMENT

In the following detailed description, reference is made to the accompanying drawings that show, by way of illustration, specific embodiments in which the invention may be practiced. These embodiments are described in sufficient detail to enable those skilled in the art to practice the invention. It is to be understood that the various embodiments of the invention, although different, are not necessarily mutually exclusive. The following detailed description is, therefore, not to be taken in a limiting sense, and the scope of the present invention is defined only by the appended claims that should be appropriately interpreted along with the full range of equivalents to which the claims are entitled.

Hereinafter, preferred embodiments of the present invention will be explained in detail with reference to the accompanying drawing so that the invention can easily practiced by those skilled in the art.

Embodiment 1

Figure 1:
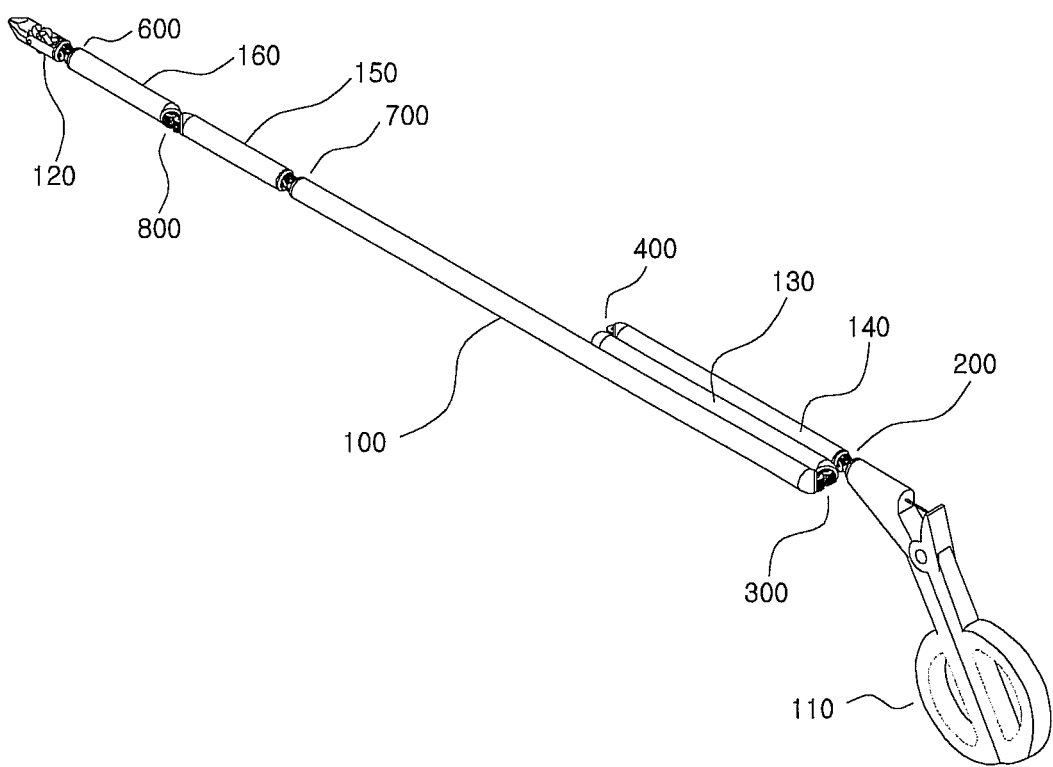
FIG. 1 is a perspective view showing the outer appearance of a tool for minimally invasive surgery in accordance with a first embodiment of the present invention.

FIG. 1 is a perspective view showing the outer appearance of a tool 1 for minimally invasive surgery, in accordance with a first embodiment of the present invention.

Referring to FIG. 1, the tool 1 for minimally invasive surgery of this embodiment includes a shaft 100 (i.e., main shaft), an adjustment handle 110, an end effector 120, first and second control shafts 130 and 140, first and second actuating shafts 150 and 160, a pitch control part 200, first and second yaw control parts 300 and 400, a pitch actuating part 600, and first and second yaw actuating parts 700 and 800.

First, as shown in FIG. 1, there is the main shaft 100, and the first and second control shafts 130 and 140 are positioned in sequence from one end of the main shaft 100, and the first and second actuating shafts 150 and 160 are positioned in sequence from the other end of the main shaft 100. At least part of the shafts have, if necessary, one or plural spaces (for example, tube-shape, lotus root-shape or spiral-shape space(s)) (not shown) inside.

In addition, the adjustment handle 110 is positioned around one end of the second control shaft 140, and the end effector 120 is positioned around one end of the second actuating shaft 160, as shown.

Hereinafter, a configuration of the tool 1 for minimally invasive surgery in accordance with the first embodiment of the present invention will be explained in further detail, with reference to the drawings.

Figure 2:
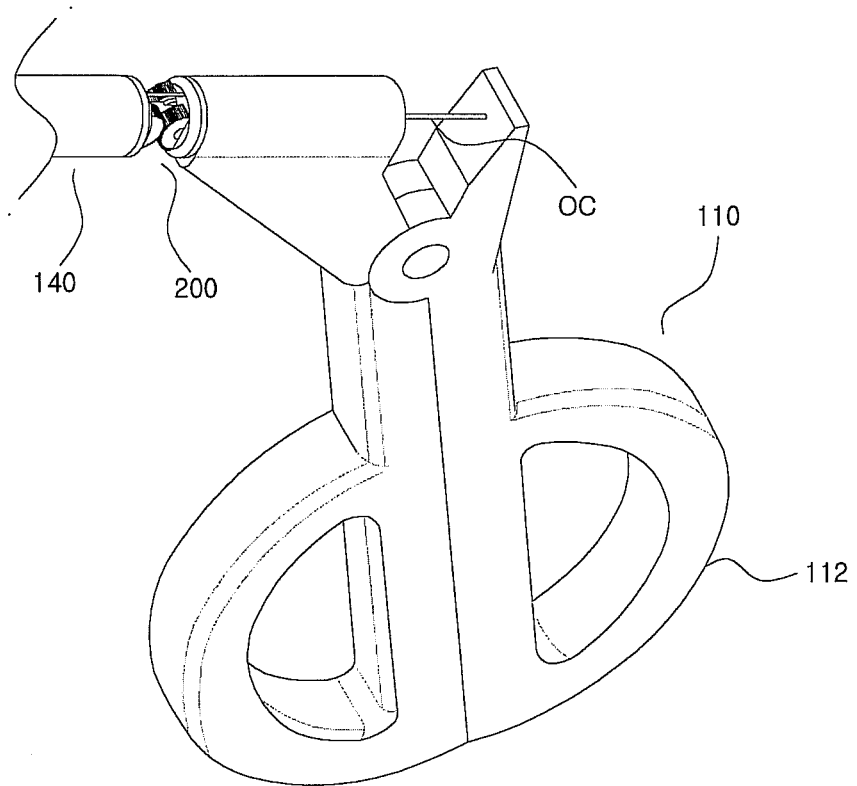
FIGS. 2 and 3 show a perspective view and a plan view of an adjustment handle in accordance with the first embodiment of the present invention.
Figure 3:
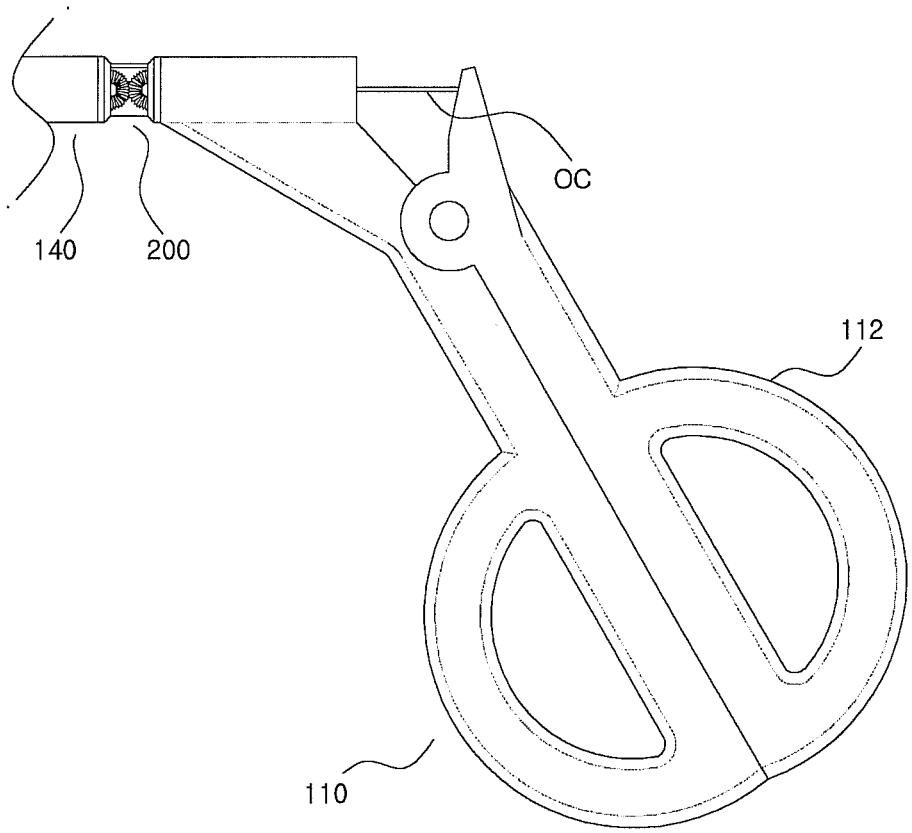

FIGS. 2 and 3 show a perspective view and a side view of the adjustment handle 110 of this embodiment, in which the adjustment handle 110 is configured in such a manner that an enclosure 112 can pull out or release an opening/closing cable OC while rotating along the rotation axis of the adjustment handle 110 (note that the opening/closing cable OC is not always necessary depending on the kind of the end effector 700, as described later). To be more specific, for the adjustment handle 110, two rods a user can grasp are connected to each other by the rotation axis, and two enclosures 112 of a semi-circular shape are formed symmetrically to each other on either end of each of the rods that are connected by the rotation axis. When one (e.g., the upper enclosure 112 as shown in the drawing) of the enclosures is opened or closed, the opening/closing cable OC may be either pulled out or released.

In addition, the adjustment handle 110 is connected to the second control shaft 140 by the pitch control part 200. A configuration of the pitch control part 200 will now be explained in detail referring to the drawings.

Figure 4:
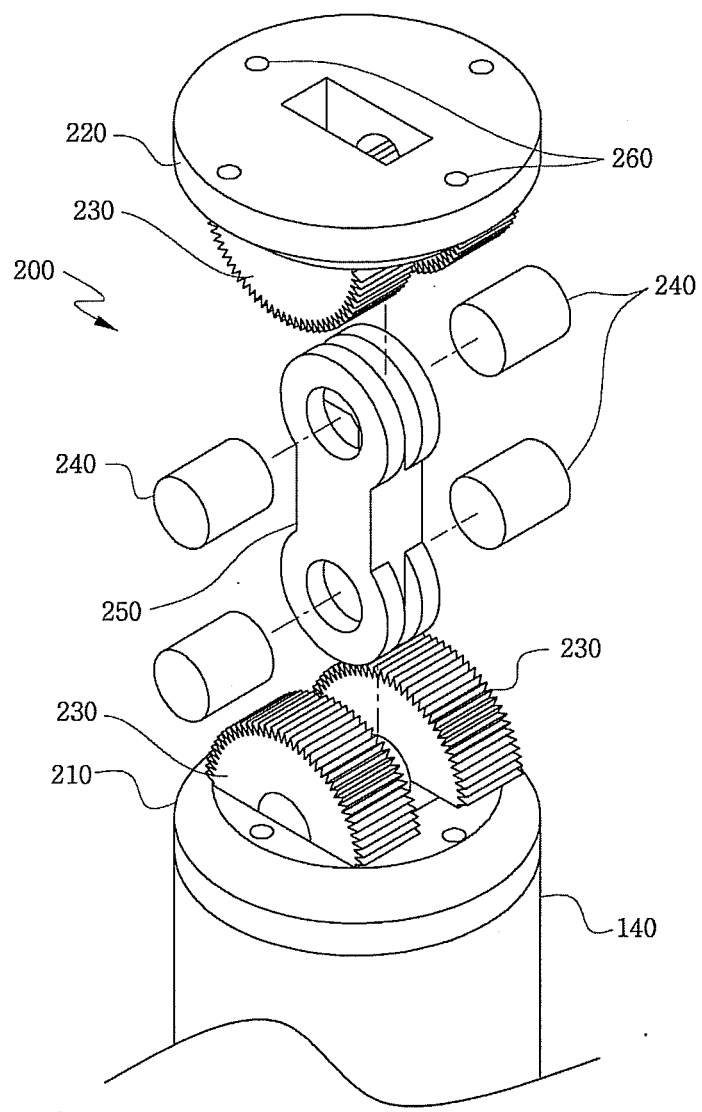
FIG. 4 is an exploded perspective view of a pitch control part in accordance with the first embodiment of the present invention.

FIG. 4 is an exploded perspective view describing the configuration of the pitch control part 200 in accordance with the first embodiment of the present invention.

As shown, as for the pitch control part 200, first and second circular plates 210 and 220 are spaced apart from each other by a predetermined distance, and two pairs of pitch adjustment gears 230 in semi-circular shape and same size are disposed on the plane perpendicular to the planes of the first and the second plates 210 and 220, parallel to each other with respect to the center axis of the first and the second plates 210 and 220.

In FIG. 4, although the first and the second plates 210 and 220 where the pitch adjustment gears 230 are disposed are in circular form occupying a minimal area, they do not need to be circular all the time but may be in any other form.

Figure 5:
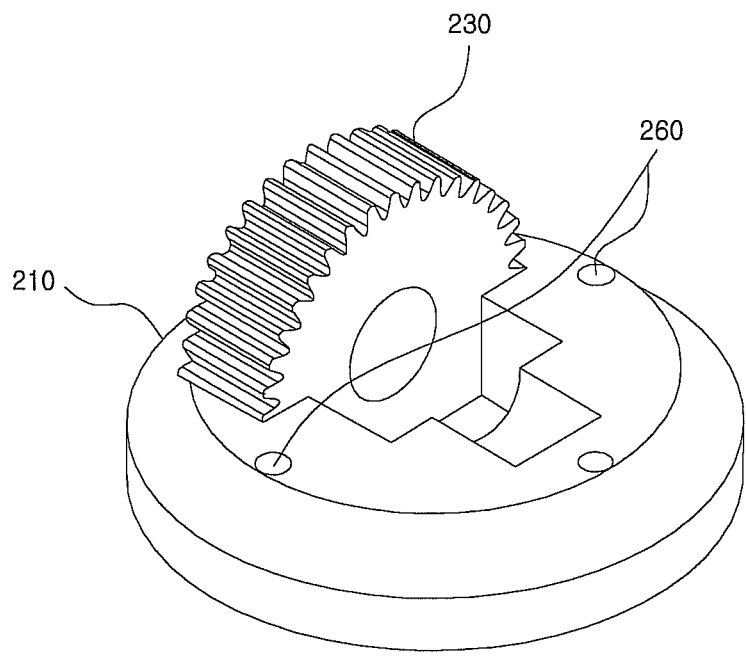
FIG. 5 shows a state where a pitch adjustment gear is disposed onto a first plate of the pitch control part in accordance with the first embodiment of the present invention.
Figure 6:
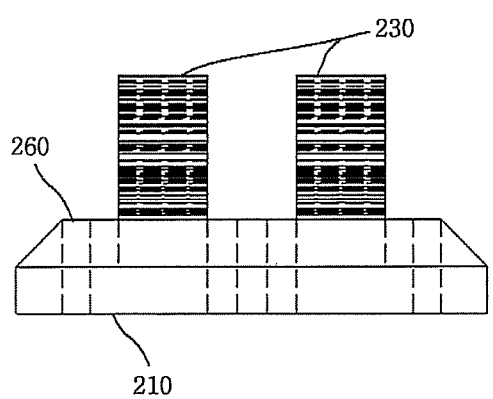
FIGS. 6 and 7 show a state where a pair of adjustment gears in a pitch direction is disposed in parallel at predetermined intervals on the first plate of the pitch control part in accordance with the first embodiment of the present invention.
Figure 7:
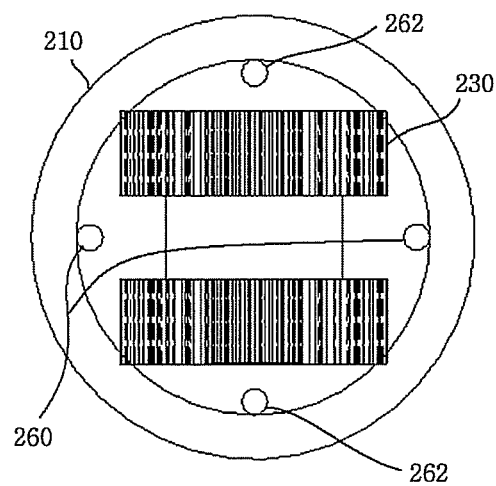

Referring further to FIGS. 5, 6 and 7, FIG. 5 shows a state where a pitch adjustment gear 230 is disposed onto the first plate 210, in accordance with the first embodiment of the present invention. In FIG. 5, even though there seems to be only one pitch adjustment gear 230 disposed on the plate, the other pitch adjustment gear 230 is just hidden from view, to clarify the status of the installation of those pitch adjustment gears 230. That is, there are actually two pitch adjustment gears 230 in pair, which is preferably disposed onto the first plate 210.

FIGS. 6 and 7 show a state in which two pitch adjustment gears 230 are disposed parallel to each other in pair at a predetermined distance, in accordance with the first embodiment of the present invention. In accordance with the first embodiment of the present invention, the operation of the pitch control part 200 is still controllable following the actuation of the adjustment handle 110 with only one pitch adjustment gear 230 deposited on one plate, but it is preferable that at least two pitch adjustment gears 230 should be provided to maintain operational stability. Meanwhile, each pair of the pitch adjustment gears 230 disposed onto the first plate 210 and the second plate 220 preferably maintains the same distance between the gears, and the pitch adjustment gears 230 disposed onto the first plate 210 and the pitch adjustment gears 230 disposed onto the second plate 220 are formed with the same pitch to intermesh.

Returning back to FIG. 4, there is a circular space in a middle point between the pitch adjustment gear 230 pairs disposed onto the first and the second plates 210 and 220, and cylindrical joint rotation axes 240 are rotatably inserted in the space. At this time, it is preferable that the central axis of the pitch adjustment gears 230 coincides with the central axis of the joint rotation axis 240.

Meanwhile, the length of the inserted joint rotation axes 240 is determined in a manner that it is longer than the thickness of each of the pitch adjustment gears 230 but not too long to make ends of the joint rotation axes 240 that are arranged in parallel come in contact with each other. Moreover, as shown, since the pitch adjustment gears 230 are formed in semi-circular shape, the middle point of each of the pitch adjustment gears 230 is located on the surface of the first and the second plates 210 and 220 accordingly.

Also, referring to FIG. 4, the semi-circular shape of the pitch adjustment gear 230 is for limiting the operation range of the adjustment handle 110 in the pitch direction of −90° to +90°. This implies that the pitch adjustment gears 230 may take another form, e.g., a sector shape, instead of the semi-circular shape, to set the operation range differently.

To make the pitch adjustment gears 230 on the first and the second plates 210 and 220 stay in intermeshed state, a first pitch link 250 may be placed between the first and the second plates 210 and 220. More details on this will now be explained with reference to FIGS. 8, 9, and 10.

Figure 8:
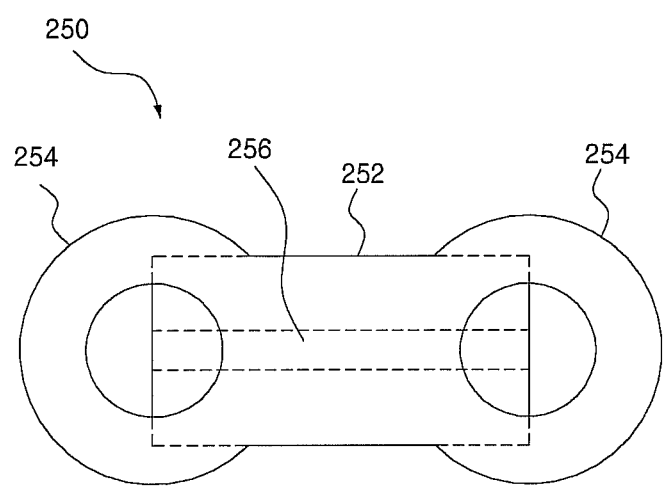
FIGS. 8, 9 and 10 show a front view, a side view, and a perspective view of the configuration of a first pitch link in accordance with the first embodiment of the present invention.
Figure 9:
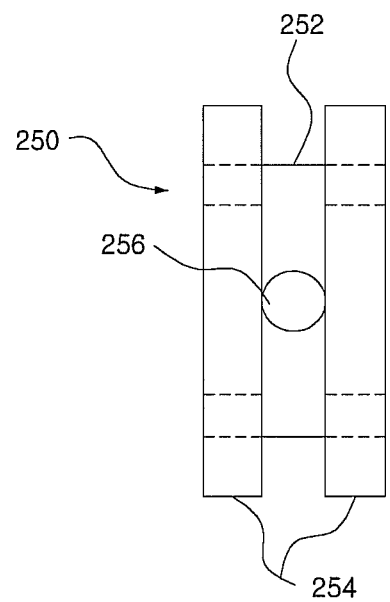
Figure 10:
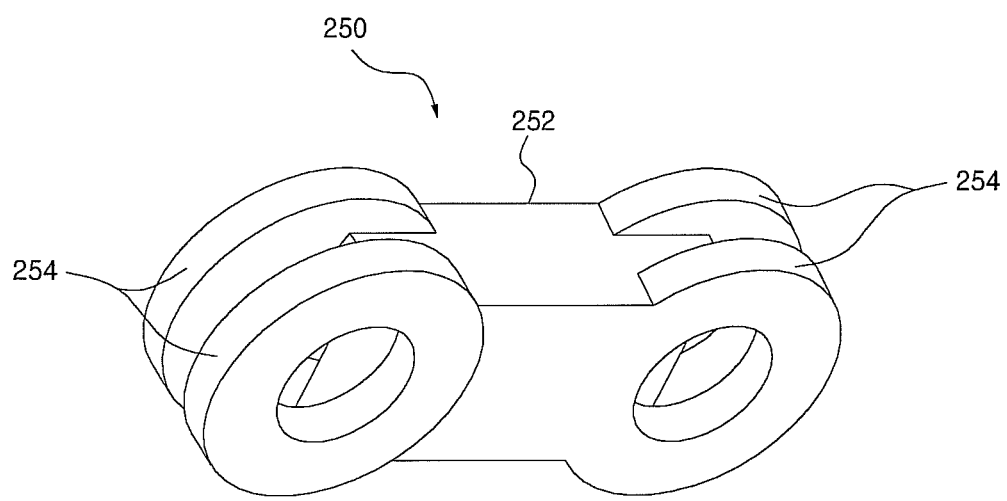

FIGS. 8, 9, and 10 show a front view, a side view, and a perspective view of a configuration of the first pitch link 250, in accordance with the first embodiment of the present invention. As shown, the first pitch link 250 includes a cuboid body 252 of predetermined length, and two pairs of rotation rings 254, each pair being formed at either end of the body with a predetermined distance between them.

In fact, one end of the joint rotation axis 240 that has been inserted in the middle point of the pitch adjustment gears 230 is inserted in the rotation ring 254 of the first pitch link 250, so as to enable the pitch adjustment gear 230 to rotate. In this way, the pitch adjustment gears 230 on the first and the second plates 210 and 220 rotate in intermeshed state, and such rotation takes place about the joint rotation axes 240 that are inserted in the rotation rings 254 on both ends of the first pitch link 250.

As depicted in FIG. 9, the body 252 of the first pitch link 250 has a through hole 256 formed along the central axis of its length direction, through which the opening/closing cable OC that connects the adjustment handle 110 and the end effector 120 passes. Preferably, the through hole 256 is positioned at the center of the body 252.

Referring back to FIGS. 4, 5, 6, and 7, there are two through holes 260 formed in each of the first and second plates 210 and 220. Preferably, the two through holes 260 are formed at angular distances of 180 degrees about the center of the first and the second plates 210 and 220, and may be used as pitch cable insert holes into which pitch cables PC are inserted. However, it should be noted that the through holes 260 in the first plate 210 are not absolutely required to be in form of insert holes, but, if necessary, they may take any other form as long as the pitch cables PC are operable therein.

Optionally, facing edges of the first and the second plates 210 and 220 may undergo edge grinding at about 45 degrees to prevent the edges of the plates from being damaged by collision with each other in their perpendicular positions.

Next, configurations of the first and second yaw control parts 300 and 400 will now be explained in detail with reference to the drawings.

As noted earlier, the second control shaft 140 connected to the adjustment handle 110 is connected to the first control shaft 130 with the second yaw control part 400, and the first control shaft 130 is connected to the main shaft 100 with the first yaw control part 300. In this way, a motion of the adjustment handle 110 in a yaw direction can be transferred.

Figure 11:
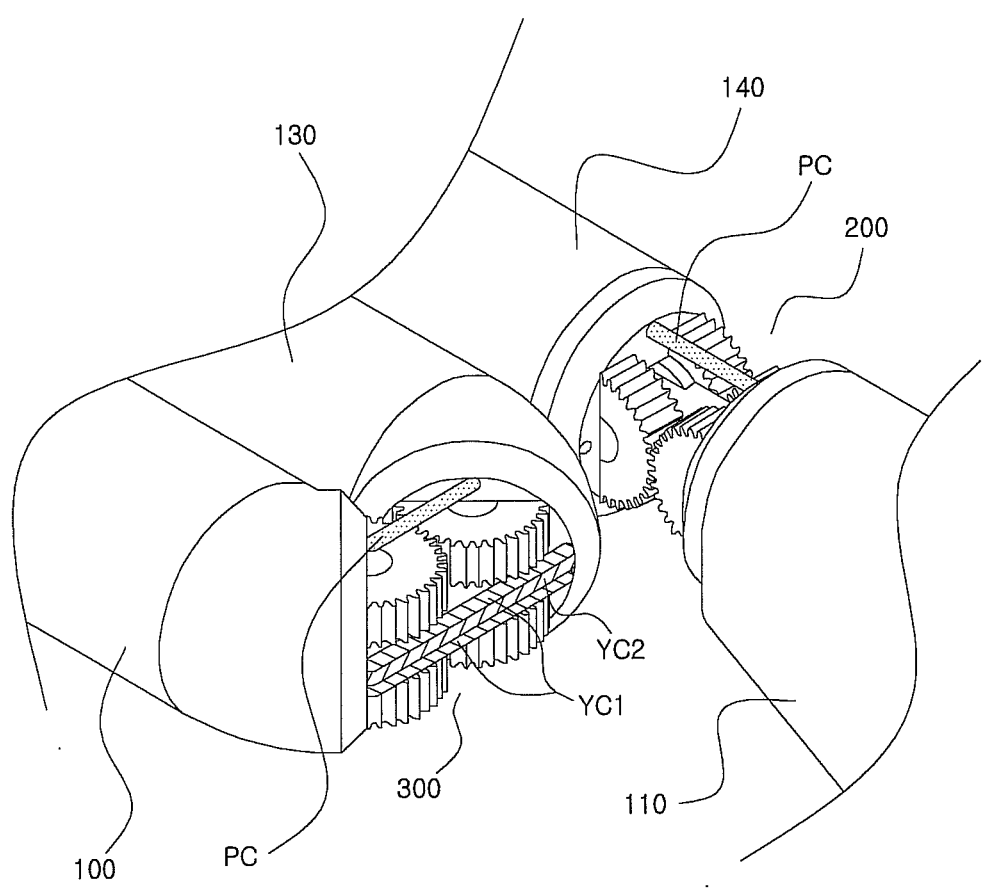
FIG. 11 is a perspective view showing a connection state between a shaft and a first control shaft by a first yaw control part in accordance with the first embodiment of the present invention.
Figure 12:
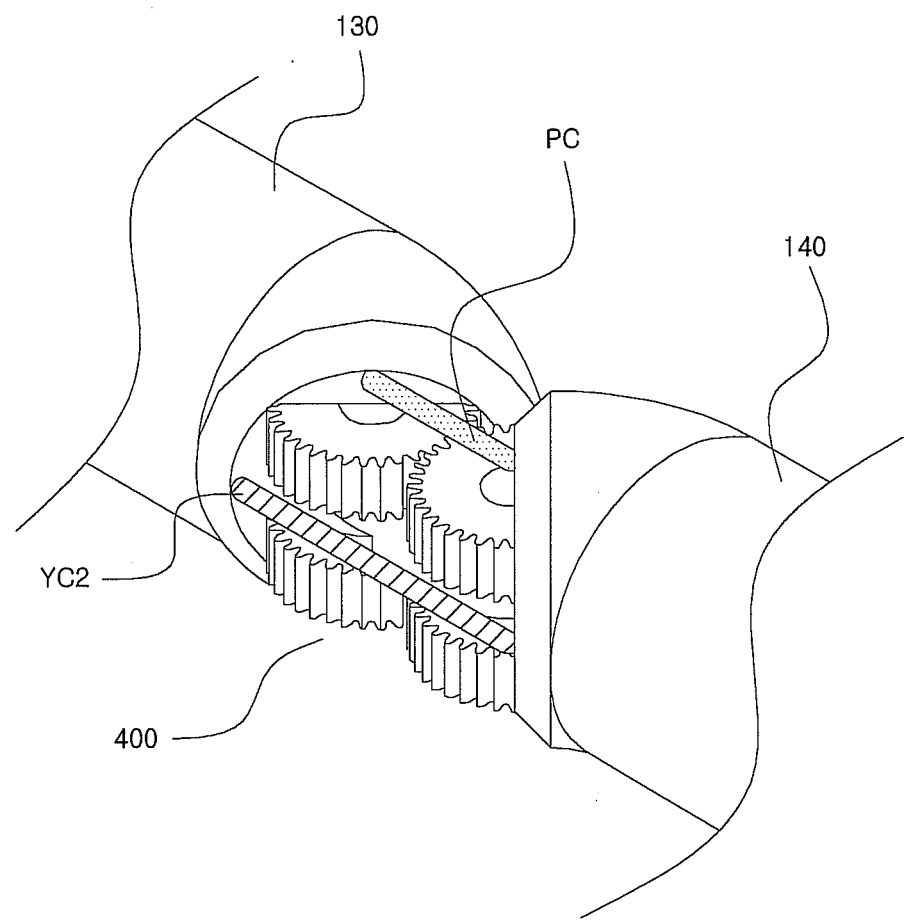
FIG. 12 is a perspective view showing a connection state between the first and the second control shafts by a second yaw control part in accordance with the first embodiment of the present invention.
Figure 13:
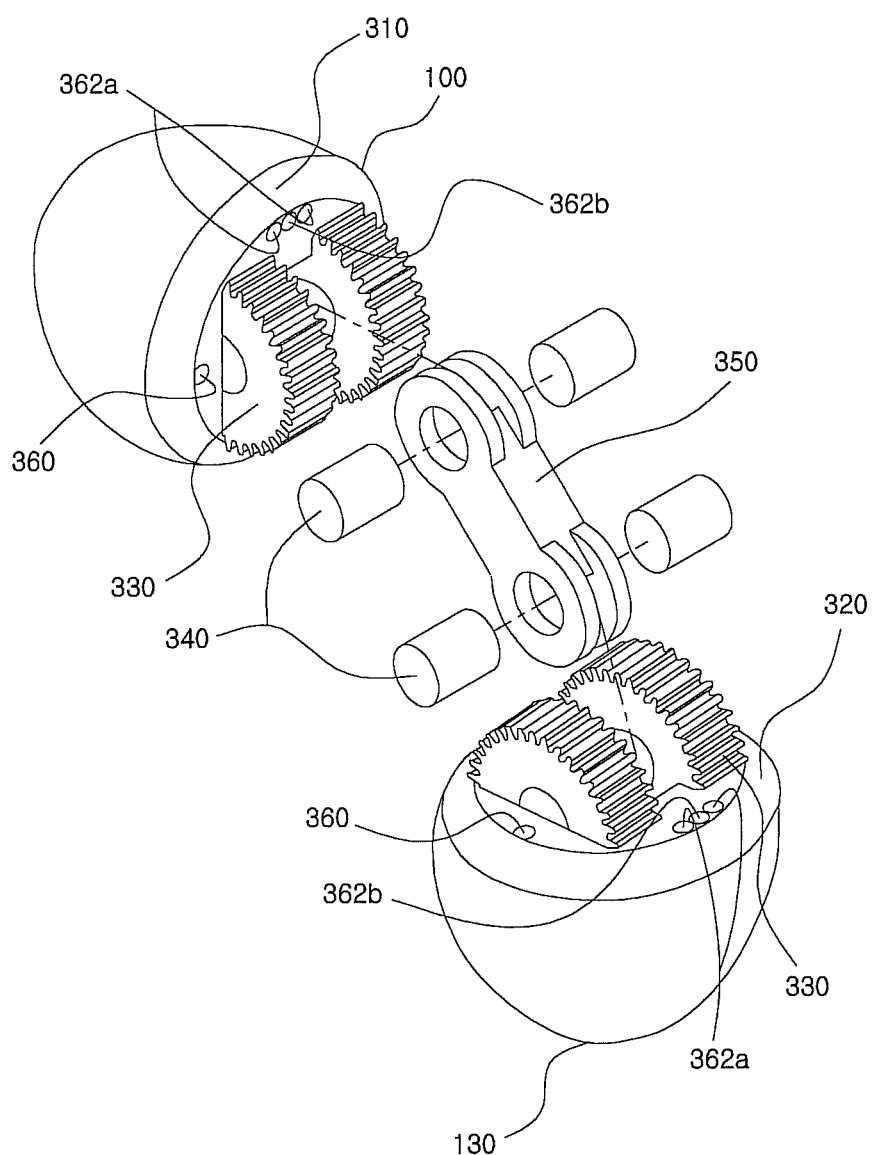
FIG. 13 is an exploded perspective view showing a configuration of the first yaw control part in accordance with the first embodiment of the present invention.
Figure 14:
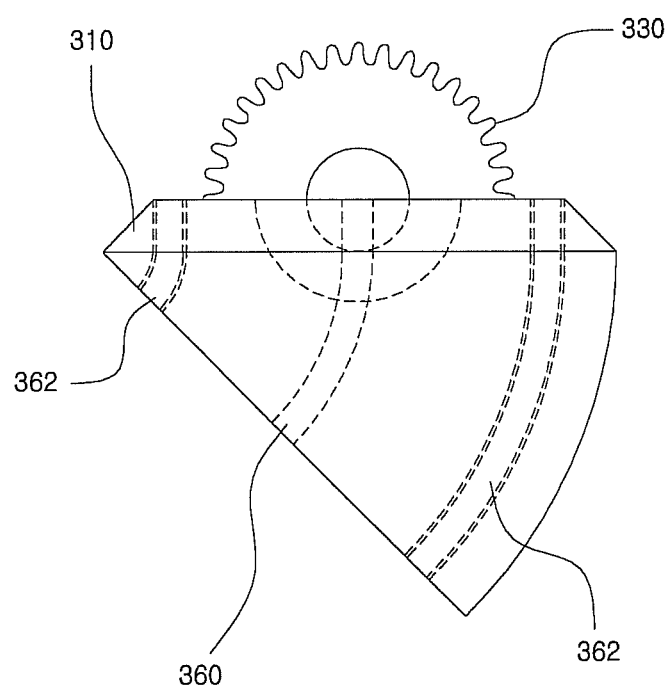
FIG. 14 is a perspective view showing a configuration of the first plate of the first yaw control part in accordance with the first embodiment of the present invention.

FIG. 11 is a perspective view showing a connection state between the main shaft 100 and the first control shaft 130 by the first yaw control part 300 in accordance with the first embodiment of the present invention, FIG. 12 is a perspective view showing a connection state between the first and second control shafts 130 and 140 with the second yaw control part 400 in accordance with the first embodiment of the present invention, FIG. 13 is an exploded perspective view showing the configuration of the first yaw control part 300 in accordance with the first embodiment of the present invention, and FIG. 14 is a perspective view showing the configuration of the first plate 310 of the first yaw control part 300 in accordance with the first embodiment of the present invention.

The first yaw control part 300 and the second yaw control part 400 are substantially configured in the same manner except that they may have slightly different configurations of cable insert holes. Therefore, the following description will mainly focus on the configuration of the first yaw control part 300.

Similar to the pitch control part 200, the first yaw control part 300 is constituted by first and second plates 310 and 320 spaced apart oppositely from each other at a predetermined distance, each plate having a pair of yaw adjustment gears 330. Two pairs of the yaw adjustment gears 330 disposed onto both sides of the first and the second plates 310 and 320 are intermeshed and they can stay in intermeshed state with the help of a first yaw link 350. Preferably, the first plate 310 and the second plate 320 meet at an angle of −90° or +90° (see the state shown in FIG. 1). However, the range of angle between the first plate 310 and the second plate 320 may vary depending on user's wants or needs.

Here, the oppositely formed first and second plates 310 and 320 of the first yaw control part 300 are preferably inclined at a predetermined angle to an orthogonal direction to the length direction of the main shaft 100 and the first control shaft 130, respectively. It is also preferable that the inclination angle is approximately 45 degrees. Again, in this case, the middle point between the yaw adjustment gears 330 of the first yaw control part is preferably positioned on the surface of the first and second plates 310 and 320.

Moreover, the first plate 310 and the second plate 320 each have first and second yaw cable insert holes 362a and 362b as shown in FIG. 13, through which a pair of first and second yaw cable YC1 and YC2 can pass.

The first yaw cable insert holes 362a formed in the first yaw control part 300 have an annular shape formed into either plate as shown in FIG. 14, such that the first yaw cable YC1 can smoothly move therein during the operation of the first yaw control part 300. Such configuration of the cable insert hole is equally applied to the second yaw control part 400.

The second yaw cable insert holes 362b are formed at angular distances of 90 degrees from the pitch cable insert hole 360 about the center of the first and the second plates 310 and 320, and the first yaw cable insert holes 362a are formed on either side of the second cable insert hole 362b. As noted earlier, in each plate, the first yaw cables YC1 pass through the first yaw cable insert holes 362a, and the second yaw cable YC2 passes through the second yaw cable insert holes 362.

The yaw control part 300 is configured substantially in the same manner as the pitch control part 200 except that the internal elements of the yaw control part 300 operate in a direction orthogonal to that of the internal elements of the pitch control part 200. So, further details on the configuration will not be provided hereinafter.

FIGS. 15, 16, 17, 18, 19 and 20 show a connection state of the main shaft 100, the first and the second actuating shafts 150 and 160, and the end effector 120. As shown, the main shaft 100 and the first actuating shaft 150 are connected with a first yaw actuating part 700, the first actuating shaft 150 and the second actuating shaft 160 are connected with a second yaw actuating part 800, and the second actuating shaft 160 and the end effector 120 are connected with a pitch actuating part 600. FIGS. 15, 16, 17, 18, 19 and 20 present a top view and/or a side view of the aforementioned elements.

Figure 15:
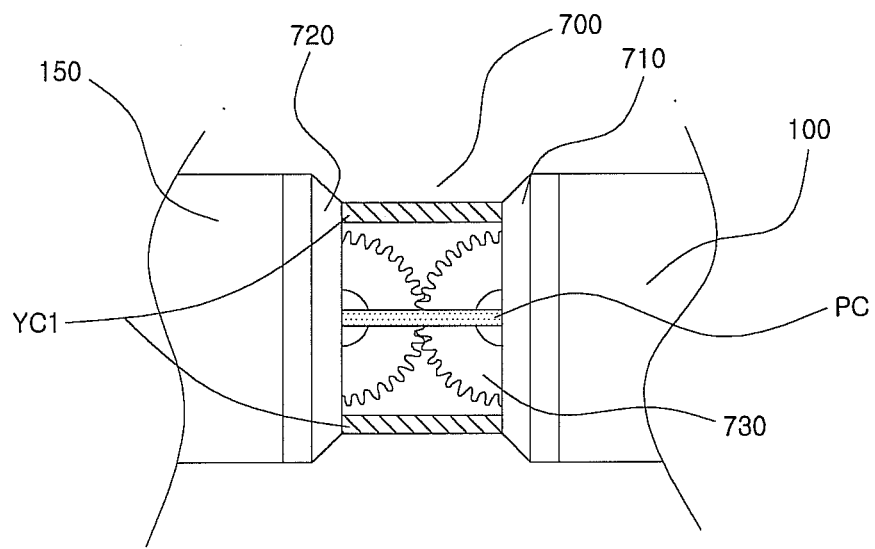
FIGS. 15, 16, 17, 18, 19 and 20 show a connection state of shaft, first and second actuating shafts, and end effector, in accordance with the first embodiment of the present invention.
Figure 16:
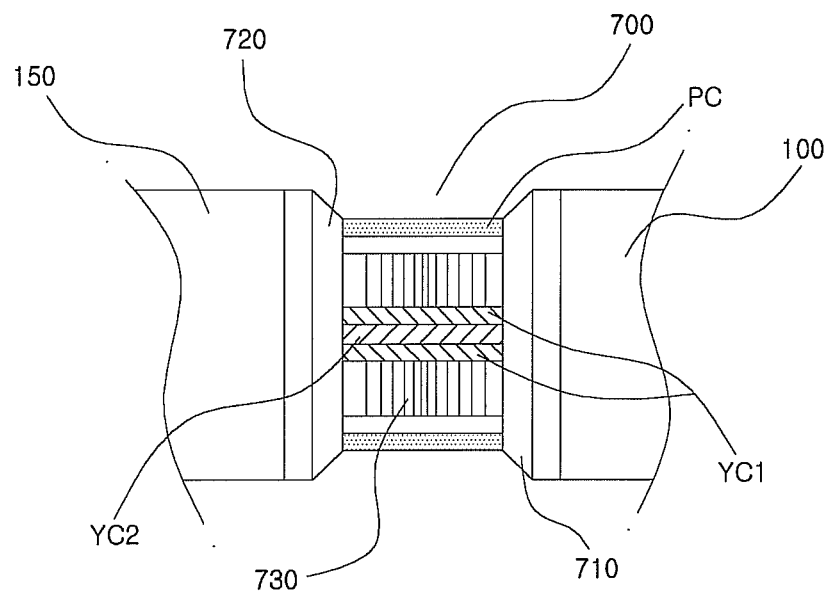

First, FIGS. 15 and 16 are described. The first yaw actuating part 700 that connects the first actuating shaft 150 to the main shaft 100 includes a first plate 710 and a second plate 720, which are positioned oppositely. Similar to the first yaw control part 300, the first yaw actuating part 700 has two pairs of the yaw direction actuating gears 730 disposed onto the first and the second plates 710 and 720 of the first yaw actuating part 700 to intermesh with each other, and the first plate 710 and the second plate 720 are connected with a second yaw link 750, so further details on this will be omitted here.

Figure 17:
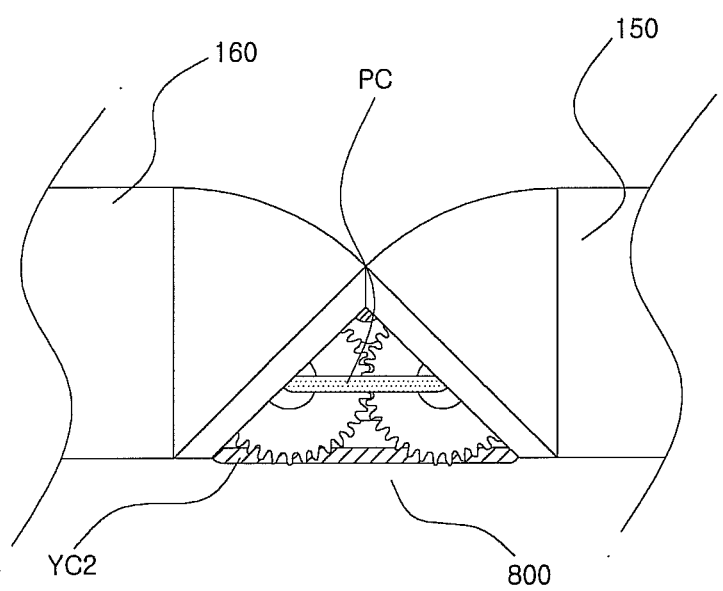
Figure 18:
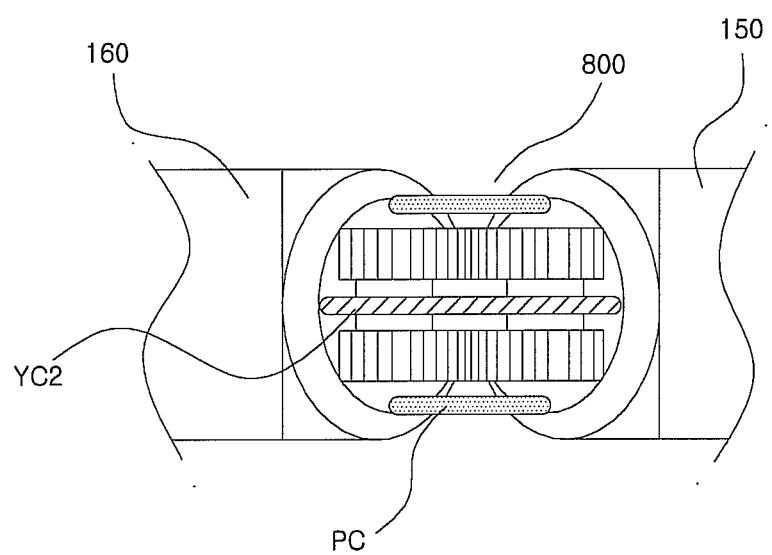

Referring next to FIGS. 17 and 18, the second yaw actuating part 800 that connects the second actuating shaft 160 to the first actuating shaft 150 has the same configuration as the second yaw control part 400, and therefore, further details on this will also be omitted here. It should be noted though that the first and the second plates of the second yaw control part 800, like those of the first or second control part 300 or 400, are preferably inclined at a predetermined angle to an orthogonal direction to the length direction of the first actuating shaft 150 and the second actuating shaft 160.

Figure 19:
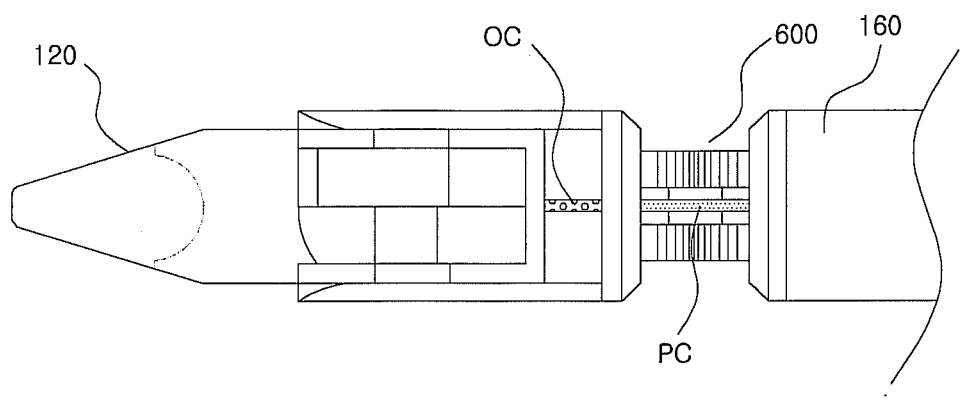
Figure 20:
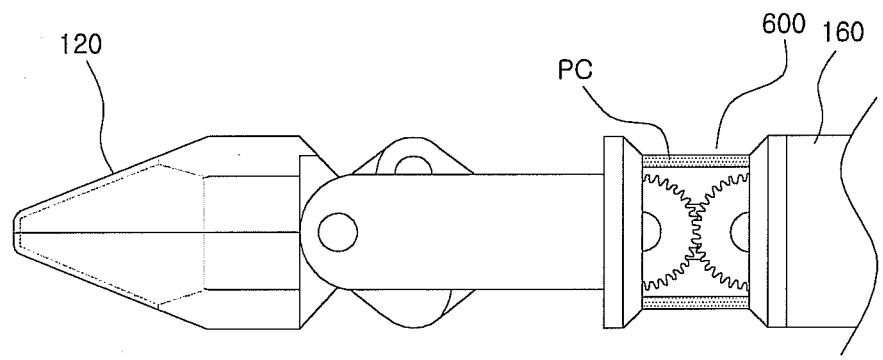

In addition, referring to FIGS. 19 and 20, the pitch actuating part 600 that connects the end effector 120 to the second actuating shaft 160 also has the same configuration as the pitch control part 200 that connects the second control shaft 140 and the adjustment handle 110, so further details on this will not be provided.

Even though some of the elements of the first and the second yaw actuating parts 700 and 800 operate in the same direction, that direction is orthogonal to the operation direction of some of the elements of the pitch actuating part 600.

In addition, the end effector 120 operates corresponding to the opening/closing operation of the adjustment handle 110, and may be used as a tool for the surgery inside the body, such as, a clamp, a gasper, scissors, a stapler, a needle holder, etc. If necessary, unlike the one shown in the drawing, the end effector 120 in accordance with the first embodiment of the present invention may be any element, such as a hook electrode, which does not need to be opened or closed.

In the following, a connection state of cables in the first embodiment of the present invention and operations of all elements relevant to the connection state will be explained further.

First, the pitch control part 200 is connected to the pitch actuating part 600 with pitch cables PC, and the first and the second control parts 300 and 400 can be connected to the first and the second yaw actuating parts 700 and 800, respectively, through the first and the second yaw cables YC1 and YC2.

In more detail, one end of each cable in the first yaw cable YC1 pair can be fixed into the first yaw cable insert holes 362a formed in the second plate 320 of the first yaw control part 300, and the other end of each cable in the first yaw cable YC1 pair can be fixed into insert holes (not shown) formed in the second plate 720 of the first yaw actuating part 700 that connects the first actuating shaft 150 to the main shaft 100.

Also, one end of the second yaw cables YC2 can be fixed into second yaw cable insert holes (not shown) formed in the second plate of the second yaw control part 400 that connects the first control shaft 130 and the second control shaft 140, and the other end of the second yaw cables YC2 can be fixed into a second yaw cable insert hole (not shown) formed in the second plate of the second yaw actuating part 800 that connects the first actuating shaft 150 and the second actuating shaft 160.

Therefore, when a user actuates the adjustment handle 110 in a pitch/yaw direction, the user's actuation (or the motion of the adjustment handle) can be transferred to the pitch actuating part 600 and the first and the second yaw actuating parts 700 and 800 through the pitch cables PC and the first and the second yaw cables YC1 and YC2, via the pitch control part 200 and the first and the second yaw control parts 300 and 400 (here, the operation in the pitch direction and the operation in the yaw direction are substantially independent of each other). At this time, the pitch cables PC are arranged passing through the inside of every shaft. To prevent entanglement of the pitch cables PC inside each shaft or to switch (invert) the direction of the cables, a guider may be installed additionally. In similar manner, the first and the second yaw cables YC1 and YC2 are arranged passing through the inside of corresponding shafts, and a guider may be installed additionally to prevent entanglement of the cables inside each shaft or to switch (invert) the direction of cables.

Although it is assumed throughout the specification that the cables are secured mainly in the through holes, it should be noted that as long as the cables operate depending on the technical aspects of the present invention, they do not necessarily have to be secured in the through holes but can be secured to other fixed elements (e.g., the plates) near the through holes.

Now, a connection state of the pitch cables PC and the first and the second yaw cables YC1 and YC2 will be discussed in detail.

As mentioned before, there are pitch cable insert holes 260 formed in the second plate 220 of the pitch control part 200. One of the pitch cable insert holes 260 that are formed in the second plate 220 of the pitch control part 200 is selected to connect and fix one end of one pitch cable PC thereto, and one pitch cable insert hole (not shown) formed in the second plate of the pitch actuating part 600 is selected to connect and fix the other end of the pitch cable PC thereto.

Similarly, another pitch cable PC is connectively secured into another pitch cable insert hole 260 formed in the second plate 220 and into another pitch cable insert hole (not shown) formed in the second plate of the pitch actuating part 600. That is, the pitch control part 200 and the pitch actuating part 600 can be connected to each other through a pair of pitch cables PC. Here, it is preferable that the pitch cables PC used for connecting the pitch control part 200 and the pitch actuating part 600 are connected parallel to each other and have the same elasticity. Alternatively, the pitch cables PC may take the form of X in the presence of the guider and the plates as noted before.

Also, the pitch cables PC are connected passing through the inside of the main shaft 100, the first and the second control shafts 130 and 140, and the first and the second actuating shafts 150 and 160 between the pitch control part 200 and the pitch actuating part 600.

The following is a detailed explanation about the second yaw cables YC2.

One end of one of the second yaw cables YC2 is connectively secured into one of the second yaw cable insert holes (not shown) formed in the second plate of the second yaw control part 400, and the other end of the second yaw cable YC2 is connectively secured into one of the second yaw cable insert holes (not shown) formed in the second plate of the second yaw actuating part 800.

Similar to the pitch cables PC described above, the second yaw cables YC2 used for connecting the second yaw control part 400 and the second yaw actuating part 800 are connected parallel to each other and may have the same elasticity.

The following is a detailed explanation about the first yaw cables YC1.

First, two pairs of yaw cables of equal length and elasticity are prepared for use as the first yaw cables YC1.

One end of each cable in the first yaw cable YC1 pair is connectively secured into the first yaw cable insert holes 362a on one side of the second plate 320 of the first yaw control part 300, and the other end of each cable in the first yaw cable YC1 pair is connectively secured into the first yaw cable insert holes on one side of the second plate of the first yaw actuating part 700. The other pair of the first yaw cables YC1 is connectively secured into the remaining, first yaw cable insert holes likewise.

Again, the two pairs of the first yaw cables YC1 used for connecting the first yaw control part 300 and the first yaw actuating part 700 are arranged substantially parallel to each other and have the same elasticity.

The operation of the tool 1 for minimally invasive surgery as configured above in accordance with one embodiment of the present invention will now be explained in more detail.

First, the tool 1 for minimally invasive surgery is arranged as shown in FIG. 1.

Next, a user who performs the minimally invasive surgery puts his or her hand in the enclosure 112 of the adjustment handle 110 that is installed at one end of the tool 1 for minimally invasive surgery and holds the adjustment handle 110.

Hereinafter, it is assumed that (+) and (−) motions in the pitch direction designate motions in the upper and lower sides about the user for convenience of explanation about the operation of the adjustment handle 110 in the pitch direction. Similarly, it is assumed that (+) and (−) motions in the yaw direction designate motions in the right and left sides about the user for convenience of explanation about the operation of the adjustment handle 110 in the yaw direction.

Figure 21:
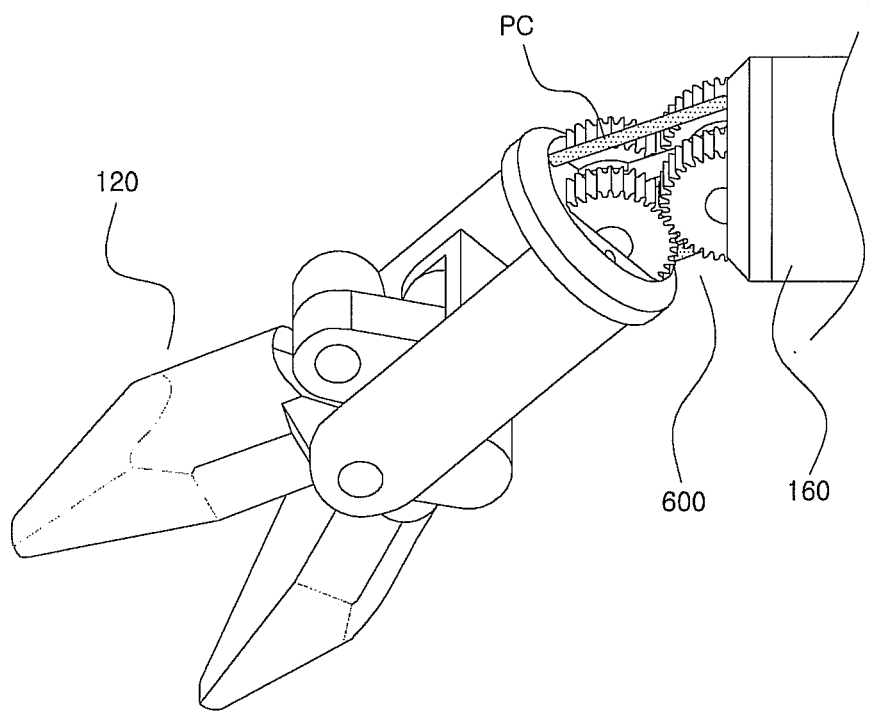
FIGS. 21, 22, 23, 24, 25 and 26 show an example of a tool for minimally invasive surgery in operation in accordance with the first embodiment of the present invention.

When the user holding the adjustment handle 110 rotates the adjustment handle 110 upwardly, the lower side cable out of the pitch cables PC having one end connectively secured into the pitch cable insert holes 260 that are formed in the first plate 210 of the pitch control part 200 is pulled, so that the upper side cable out of the pitch cables PC is released in opposite direction, thereby making the end effector 120 rotate downwardly as shown in FIG. 21. Needless to say, when the user rotates the adjustment handle 110 in opposite direction, the end effector 120 will rotate in opposite direction as well, and an amount of rotation of the adjustment handle 110 is proportional to that of the end effector 120.

Figure 22:
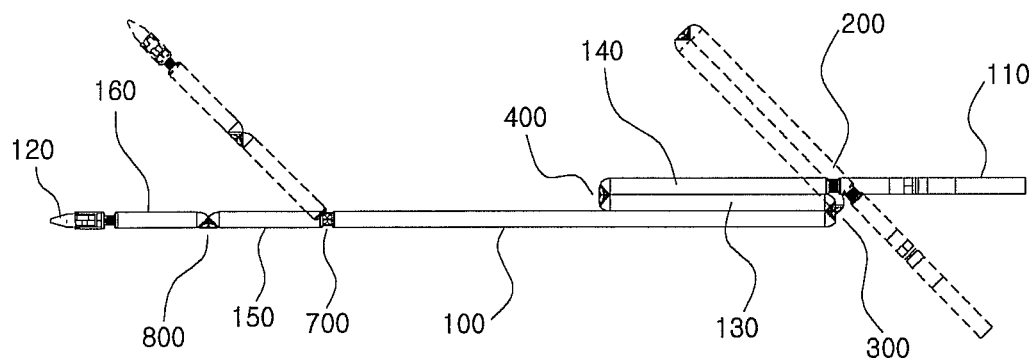

Meanwhile, when the user holding the adjustment handle 110 rotates the adjustment handle 110 to the left as shown in FIG. 22, the second control shaft 140 rotates, together with the first control shaft 130 connected with the second yaw control part 400, to the right.

Figure 23:
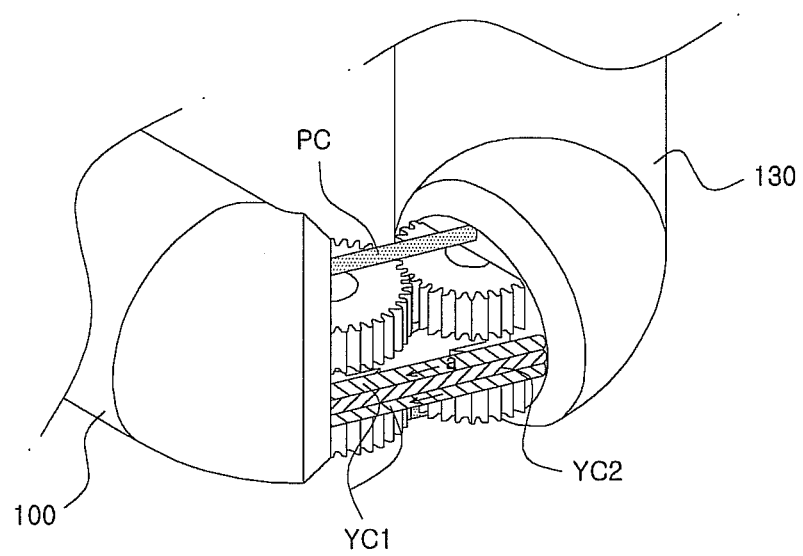

When the first and the second control shafts 130 and 140 rotate and face the right side, the first yaw cables YC1 on one side of the first yaw cables YC1, one end of each of which is connectively secured into the first yaw cable insert holes 362a formed in the second plate 320 of the first yaw control part 300, operate in 'a' direction as shown in FIG. 23. Accordingly, the first yaw cables YC1 on the other side operate in the opposite direction of the 'a' direction.

Since the other end of each of the first yaw cables YC1 is connectively secured into the first yaw cable insert holes (not shown) formed in the second plate of the first yaw actuating part 700, the first actuating shaft 150 rotates to the right by the first yaw cables YC1 that are pulled in the opposite direction of the 'a' direction. At this time, the second actuating shaft 160 and the end effector 120 connected to the first actuating shaft 150 operate in a way that their central axes stay aligned with the central axis of the first actuating shaft 150.

At this time, the first control shaft 130 and the first actuating shaft 150 operate in the same yaw direction and, each rotates at an amount proportional to the other.

Figure 24:
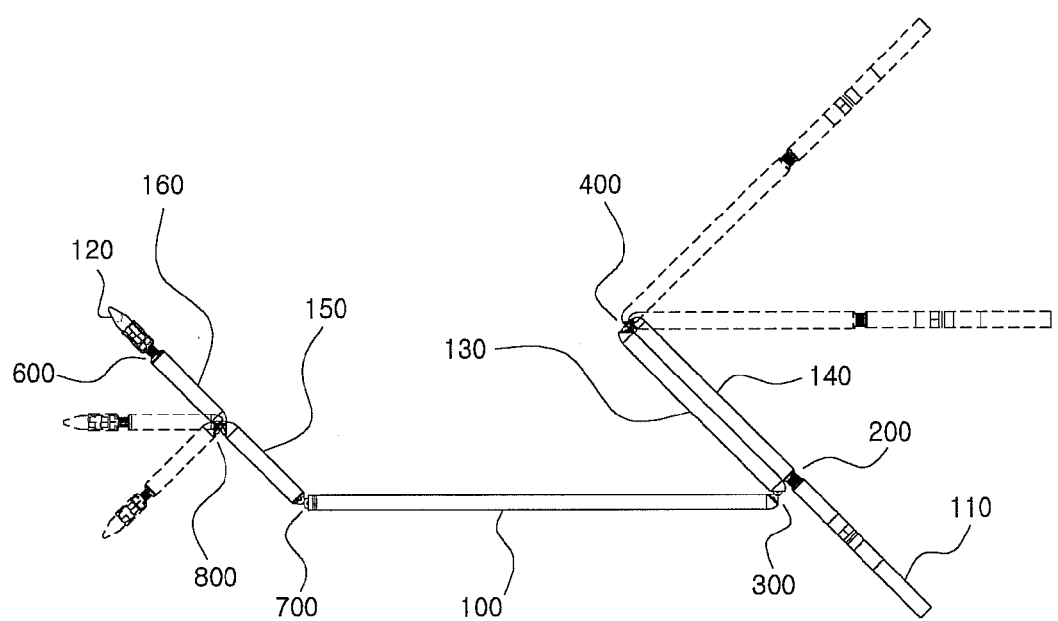

Thus, as shown in FIG. 24, the second control shaft 140 connected to the adjustment handle 110 can rotate to the right.

Figure 25:
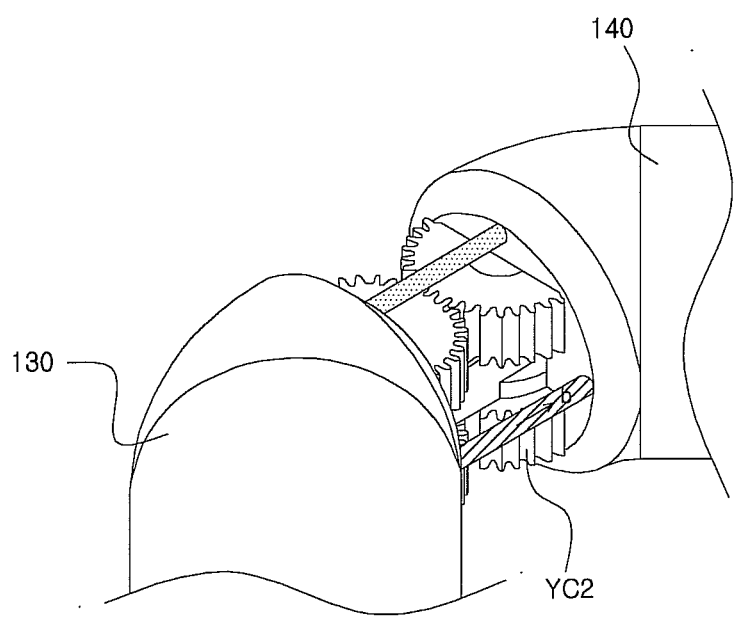

When the adjustment handle 110 and the second control shaft 140 move to the right, as shown in FIG. 25, the second yaw cable YC2 on the left-hand side out of the second yaw cables YC2, one end of which is connected to the second yaw cable insert hole (not shown) in the second plate of the second yaw control part 400, operates in 'b' direction, and the second yaw cable YC2 on the right-hand side is pulled in the opposite direction of the 'b' direction.

Since the other end of the second yaw cable YC2 is connectively secured into the second yaw cable insert hole (not shown) formed in the second plate of the second yaw actuating part 800, the second actuating shaft 160 rotates to the left by the second yaw cable YC2 that is pulled in the 'b' direction. At this time, the end effector 120 connected to the second actuating shaft 160 operates in a way that its central axis stays aligned with the central axis of the second actuating shaft 160.

Here, the second control shaft 140 and the second actuating shaft 160 operate in the same yaw direction and, each rotates at an amount proportional to the other.

Figure 26:
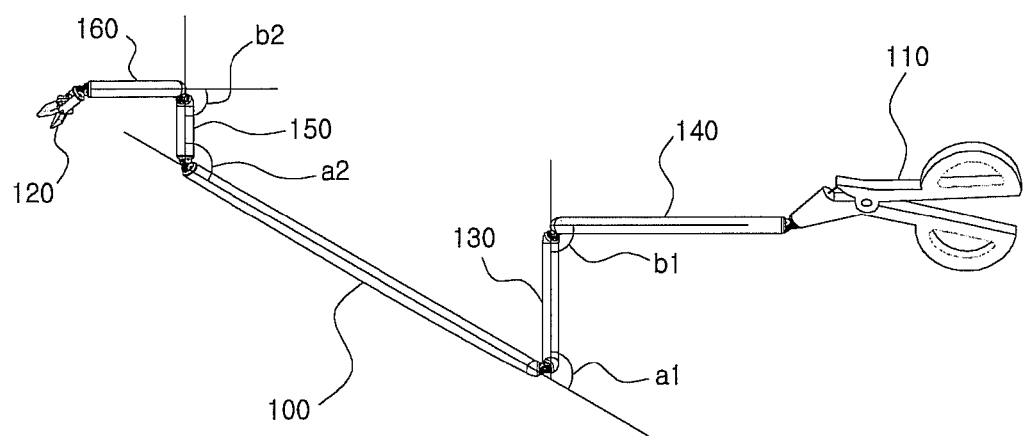

Therefore, as shown in FIG. 26, a yaw angle a1 between the main shaft 100 and the first control shaft 130 is equal to a yaw angle a2 between the main shaft 100 and the first actuating shaft 150. Further, a yaw angle b1 between the first control shaft 130 and the second control shaft 140 is equal to a yaw angle b2 between the first actuating shaft 150 and the second actuating shaft 160. As such, the user can control the operation of the end effector 120 according to the user's intention.

If the adjustment handle 110 is actuated in the opposite direction, it is obvious that the end effector 120 will operate in the opposite direction.

Meanwhile, if the user closes the adjustment handle 110 while leaving the end effector 120 in a state where it faces a desired direction with the control over the adjustment handle 110, the closing motion of the adjustment handle 110 is transferred to the end effector 120 via the opening/closing cable OC, thereby causing the end effector 120 to close. On the contrary, if the user opens the adjustment handle 110, the end effector 120 will return to its original open state with the help of the resilient force from restoration springs (not shown) installed therein. If needed, the user may use the end effector 120 with an opening/closing function for surgery.

While it is described that the end effector 120 is opened following the opening of the adjustment handle 110 by the user, it is also possible to configure in such a way that they operate in an opposite manner depending on the kind of the end effector 120 used. Also, as discussed earlier, it is to be understood that the opening/closing cable OC may be pulled either by the upper side enclosure 112 or by the lower side enclosure 112 out of the two enclosures 112 of the adjustment handle 110.

So far, the operation of the minimally invasive surgical tool 1 in accordance with the present invention has been explained in order of the operation in the pitch direction, the operation in the yaw direction, and the opening direction of the end effector for convenience of explanation, but it may be performed in a different order from the one mentioned above, or two or more operations may be performed at the same time. Either way, the operational principle of the minimally invasive surgical tool 1 in accordance with the present invention remains unchanged.

Meanwhile, if all of the adjustment gears used for the control parts and the actuating parts are of the same size, the displacement amount of the adjustment handle 110 and the displacement amount of the end effector 120 are at the ratio of 1:1. This ratio can be varied by using different sized adjustment gears. That is, the displacement amount of the adjustment handle 110 and the displacement amount of the end effector 120 may be set differently from each other, by varying the size of the adjustment gears used for the control/actuating parts.

For instance, if the pitch adjustment gear 230 of the pitch control part 200 has a larger diameter than a pitch direction adjustment gear (not shown) of the pitch actuating part 600, the pitch direction adjustment gear (not shown) of the pitch actuating part 600 rotates at a greater angle than the user operated motion, so the end effector 120 eventually rotates more than the adjustment handle 110. Needless to say, in the opposite case, the displacement amount of the end effector 120 is smaller than the displacement of the adjustment handle 110.

Embodiment 2

Figure 27:
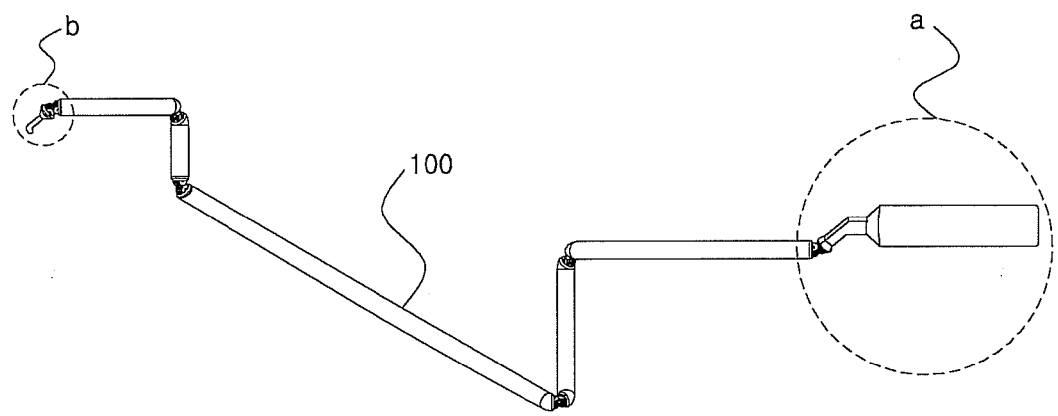
FIG. 27 is a perspective view showing the outer appearance of a tool for minimally invasive surgery in accordance with a second embodiment of the present invention, and FIGS. 28 and 29 respectively show detailed views of a area and b area in FIG. 27.
Figure 28:
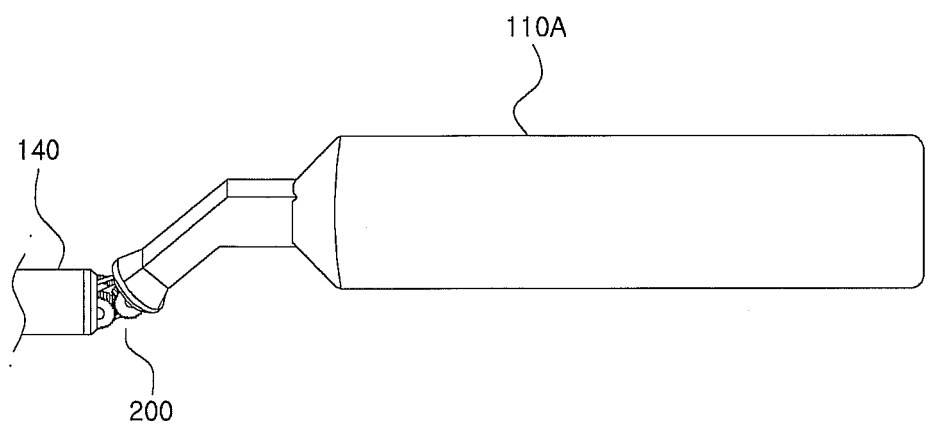
Figure 29:
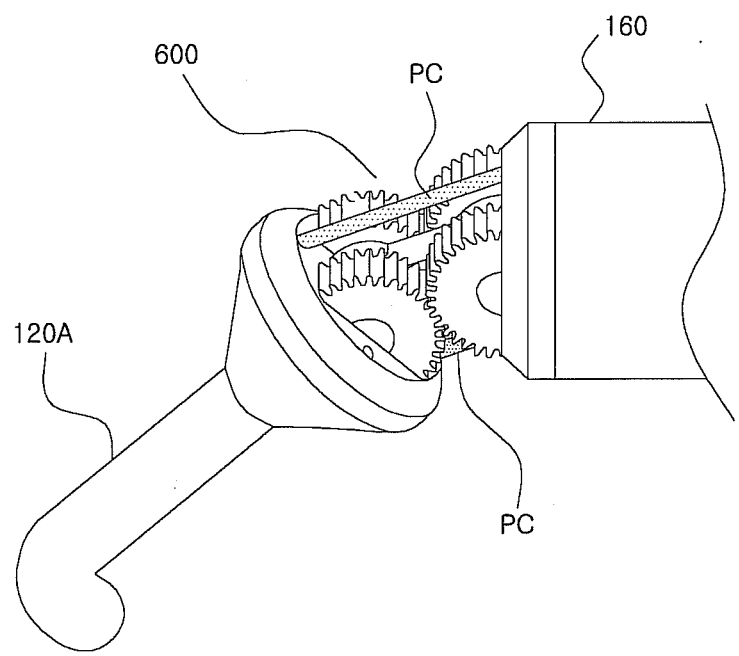

FIG. 27 is a perspective view showing the outer appearance of a tool for minimally invasive surgery in accordance with a second embodiment of the present invention, and FIGS. 28 and 29 show detailed views of a area and b area in FIG. 27, respectively. In explaining this embodiment, the same reference numerals will be used for the same elements as the first embodiment, and a detailed description thereon will be omitted here.

In accordance with the second embodiment of the present invention, an adjustment handle 110A for controlling the operation of an end effector 120A (preferably a hook electrode) can be connected to one end of a second control shaft 140 by a pitch control part 200, and the end effector 120A can be connected to one end of a second actuating shaft 160 by a pitch actuating part 600.

Unlike the first embodiment, the end effector 120A of this embodiment can have a bar shape (or any other shape, e.g., a ring shape, depending on user's needs as long as the opening/closing operations are not accompanied).

In this embodiment, connections between the adjustment handle 110A, the end effector 120A, and many cables are basically identical to those in the first embodiment, except that an opening/closing cable is not required. Thus, the configuration and operation of the minimally invasive surgical tool in accordance with this embodiment will be omitted here for simplicity.

Embodiment 3

Figure 30:
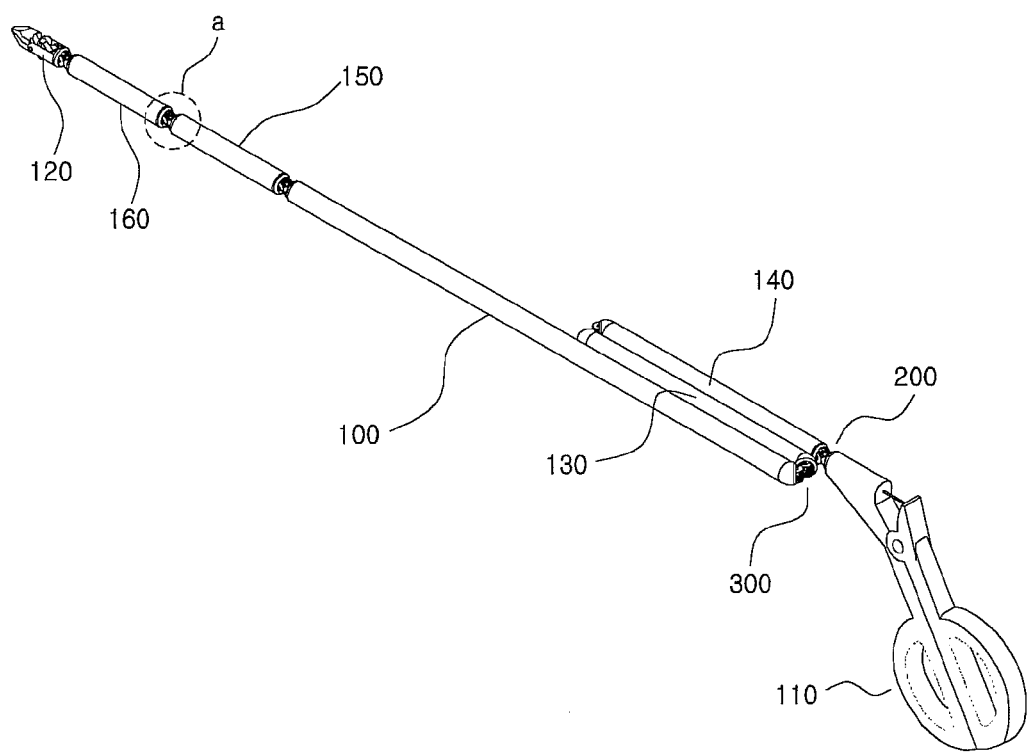
FIG. 30 is a perspective view showing the outer appearance of a tool for minimally invasive surgery in accordance with a third embodiment of the present invention.
Figure 31:
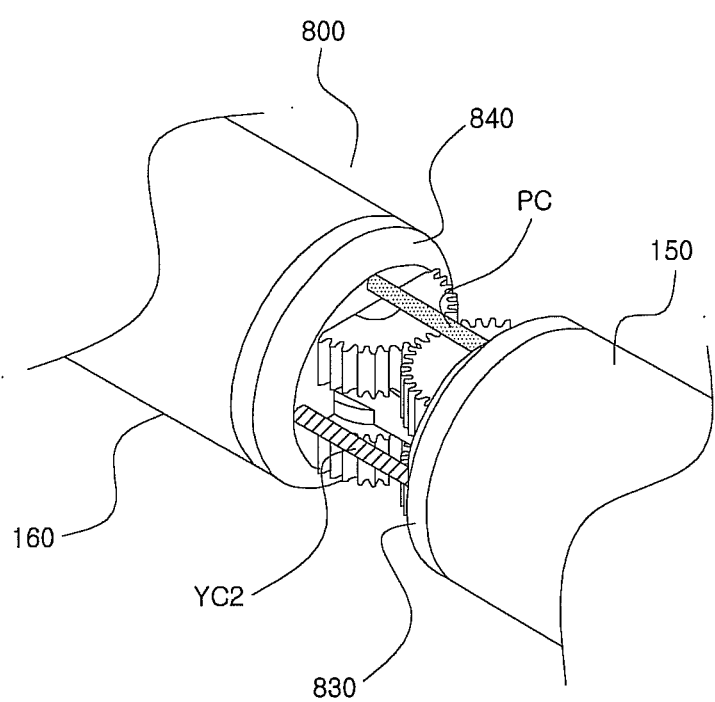
FIG. 31 shows a detailed view of a area in FIG. 30.

FIG. 30 is a perspective view showing the outer appearance of a tool for minimally invasive surgery in accordance with a third embodiment of the present invention, and FIG. 31 shows a detailed view of a area in FIG. 30.

Figure 32:
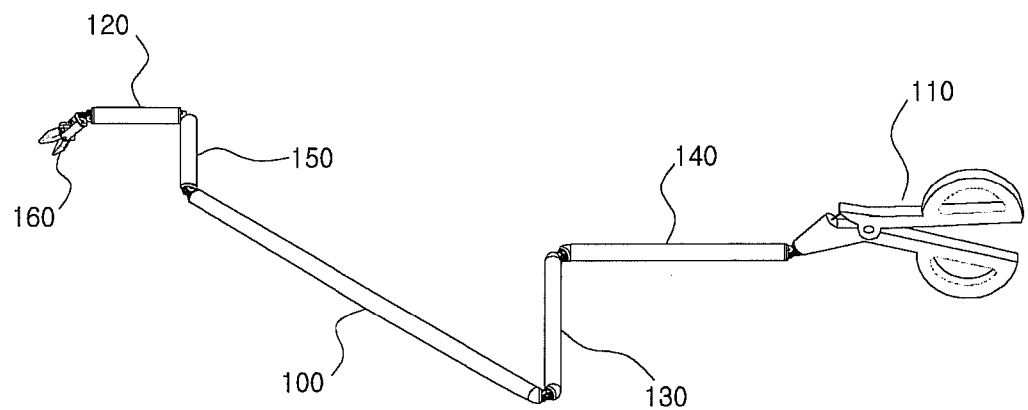
FIGS. 32 and 33 show an example of a tool for minimally invasive surgery in operation in accordance with the third embodiment of the present invention.
Figure 33:
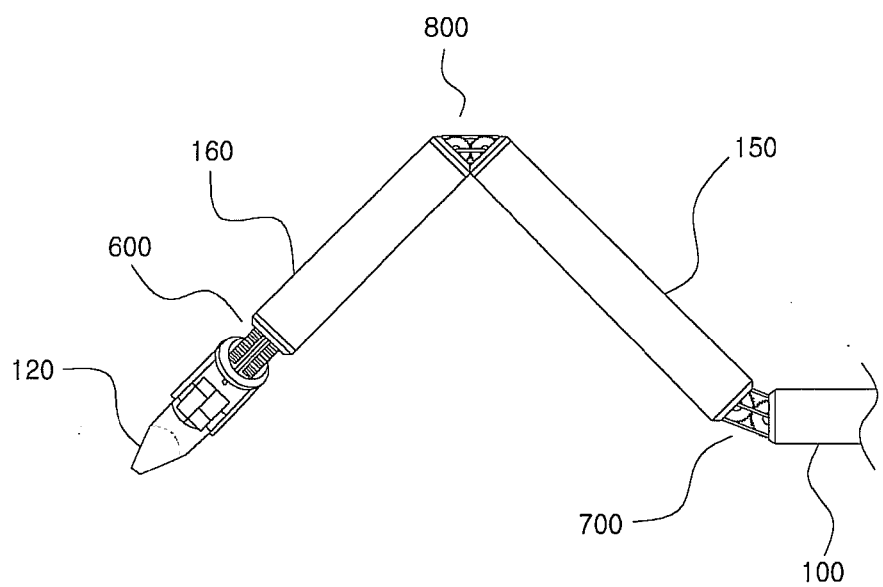

This embodiment is basically identical to the first embodiment in its configuration and operation, except that, as shown in FIG. 31, first and second plates 830 and 840 which constitute a second yaw actuating part 800 for connecting first and second actuating shaft 150 and 160 are not tilted but parallel to each other similarly to a pitch actuating part 200. So no detailed description on the configuration and operation will be provided here. In accordance with this embodiment, however, as depicted in FIG. 32 and FIG. 33, since the first and the second plates 830 and 840 are disposed parallel to each other, it can be easier to insert the first actuating shaft 150 through a trocar than in the first embodiment.

In addition, in this embodiment, an end effector with no opening/closing function may be used as in the second embodiment. Also, an adjustment handle with no opening/closing function may be used. Depending on user's needs, the end effector may take any other form (e.g., a ring shape) as long as it will not open or close. This aspect can be applied not only to this embodiment, but also to all embodiments to be described later.

Embodiment 4

Figure 34:
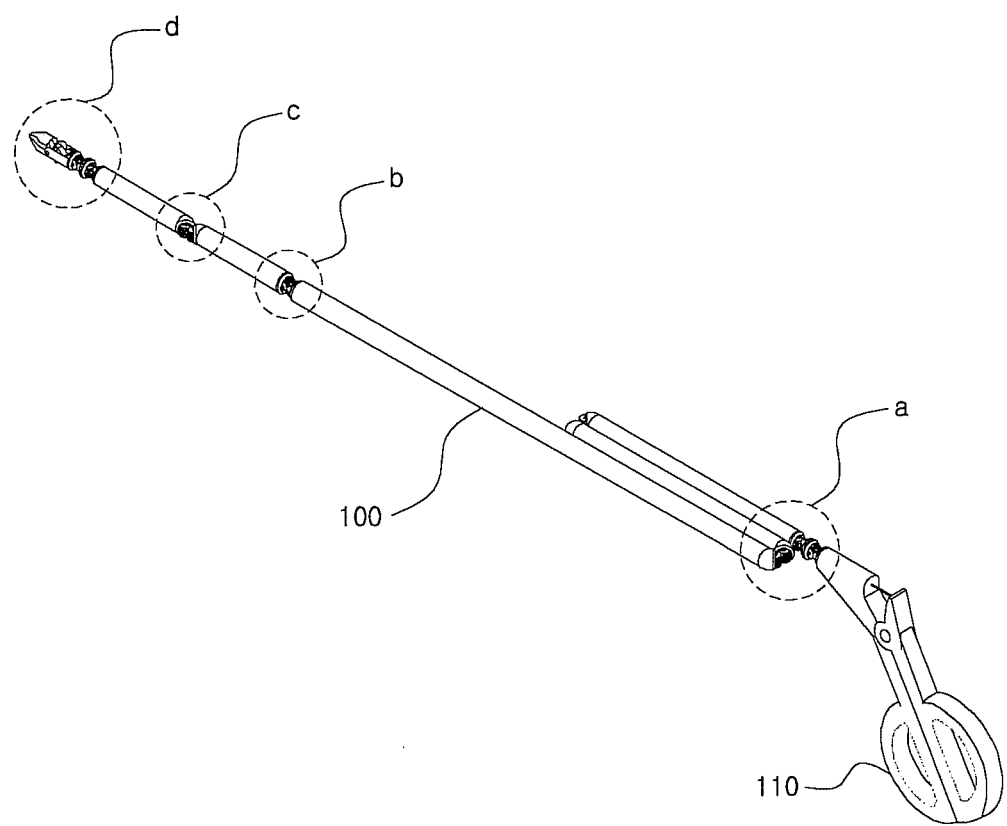
FIG. 34 is a perspective view showing the outer appearance of a tool for minimally invasive surgery in accordance with a fourth embodiment of the present invention.

FIG. 34 is a perspective view showing the outer appearance of a tool for minimally invasive surgery in accordance with a fourth embodiment of the present invention, and FIGS. 35 to 38 show detailed views of a, b, c and d areas in FIG. 34, respectively.

Referring to the drawings, a third yaw control part 500 is additionally installed near a pitch control part 200 that connects an adjustment handle 110 and a second control shaft 140, and a third yaw actuating part 900 is additionally installed near a pitch actuating part 600 that connects an end effector 120 and a second actuating shaft 160. Besides, first, second and third yaw cables YC1, YC2 and YC3 are installed to connect first, second and third yaw control parts 300, 400 and 500 and first, second and third yaw actuating parts 700, 800 and 900, respectively.

Now, the configuration of the minimally invasive surgical tool of the fourth embodiment will be explained in detail with reference to the drawings.

Figure 35:
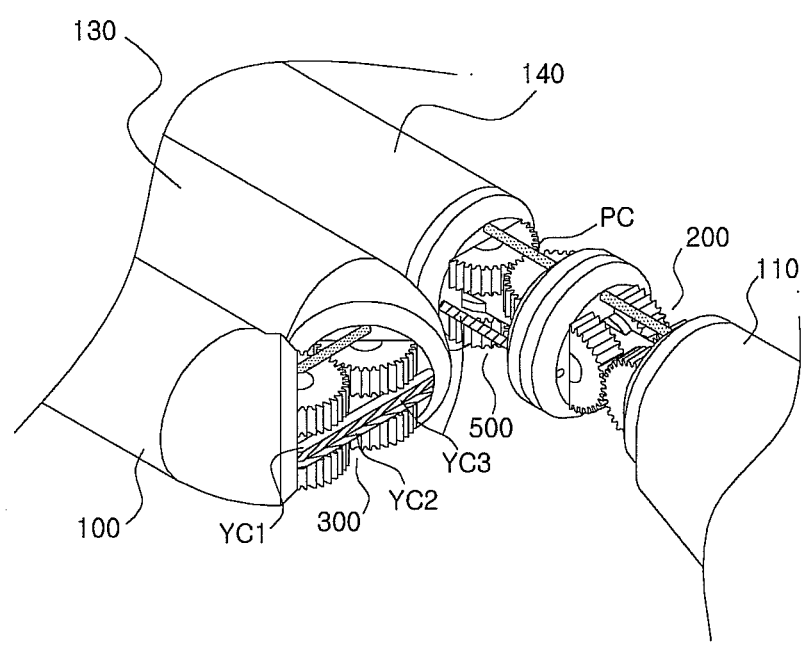
FIGS. 35 to 38 show detailed views of a, b, c and d areas in FIG. 34, respectively.

Referring first to FIG. 35, the third yaw control part 500 is installed near the pitch control part 200 that is connected to the adjustment handle 110, and the second control shaft 140 is connected to the pitch control part 200 by the third yaw control part 500. The third yaw control part 500 is disposed in a manner that some of its elements operate in a direction orthogonal to the operation direction of some of elements of the pitch control part 200. Since the third yaw control part 500 has substantially the same configuration as the pitch control part 200, it will not be explained in detail here.

Meanwhile, as shown, three yaw cables YC1, YC2 and YC3 may be connected across the first yaw control part 300. Among them, the third yaw cables YC3 are connected across all of the three yaw control parts 300, 400 and 500, while the second yaw cables YC2 are connected across only the first and the second yaw control parts 300 and 400 and the first yaw cables YC1 are connected across only the first yaw control part 300.

Figure 36:
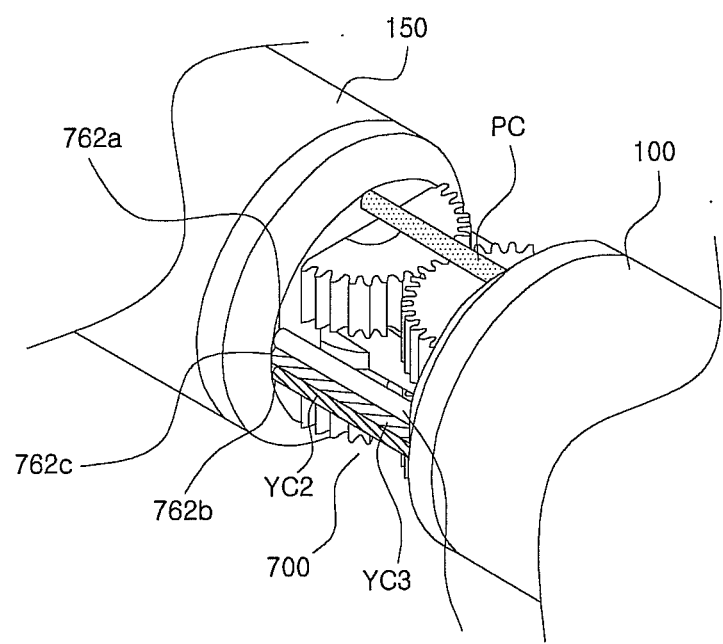
Figure 37:
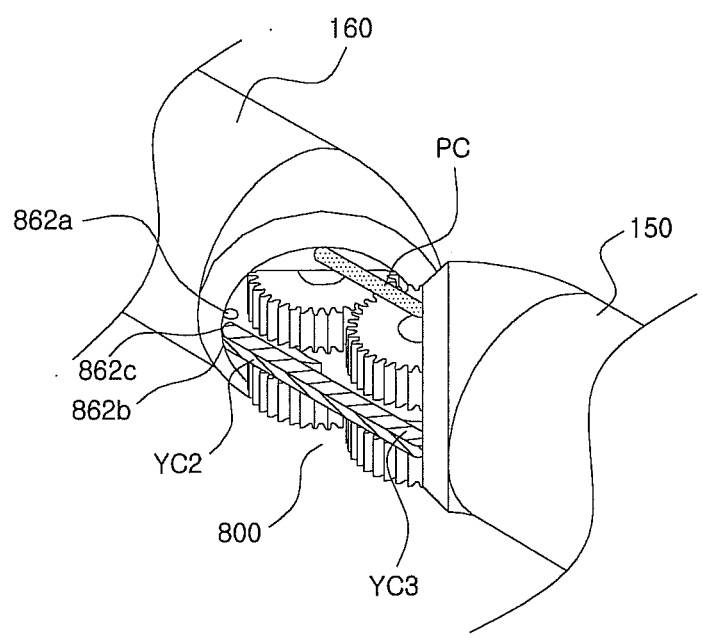

The yaw actuating part can also be configured correspondingly. For instance, as shown in FIG. 36, the main shaft 100 and the first actuating shaft 150 can be connected by the first yaw actuating part 700, wherein all of the three yaw cables YC1, YC2 and YC3 are connected across the first yaw actuating part 700. Since the first yaw actuating part 700 is configured in the same manner with the previous embodiments, a detailed description on its configuration will be omitted here. FIG. 37 shows that the first actuating shaft 150 and the second actuating shaft 160 are connected by the second yaw actuating part 800. As in the second yaw control part 400, only the second and the third yaw cables YC2 and YC3 cross the second yaw actuating part 800.

Figure 38:
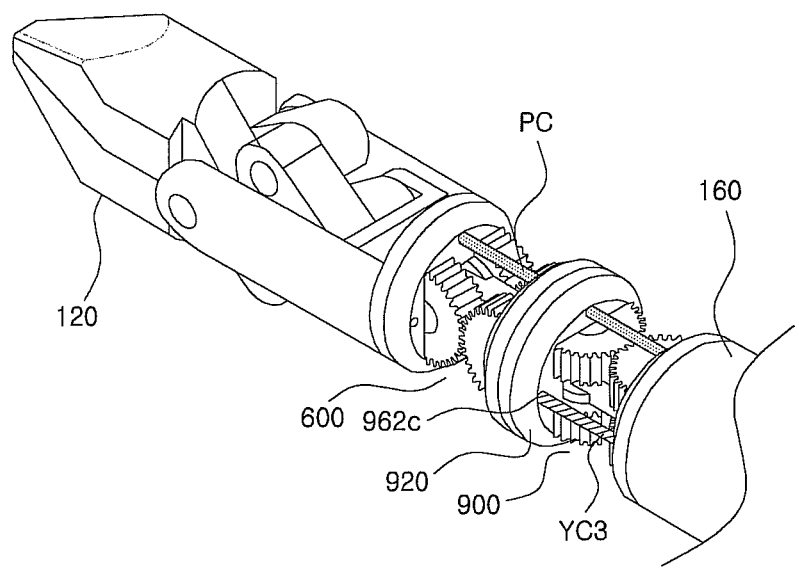

Lastly, FIG. 38 shows that the third yaw actuating part 900 is installed near the pitch actuating part 600 which is connected to the end effector 120, and the second actuating shaft 160 and the pitch actuating part 600 are connected to each other by the third yaw actuating part 900. In addition, as in the third yaw control part 500, only the third yaw cables YC3 crosses the third yaw actuating part 900. Here, the third yaw actuating part 900 is disposed in a manner that some of its elements operate in a direction orthogonal to the operation direction of some of elements of the pitch actuating part 600. Since the third yaw actuating part 900 has substantially the same configuration as the pitch actuating part 600, it will not be explained in detail here.

The following are more details on characteristic configuration of yaw cables in this embodiment.

In this embodiment, it can be seen that a motion of the adjustment handle 110 is transferred to the end effector 120 via pitch cable PCs and the first to third yaw cables YC1, YC2 and YC3.

First, both ends of the pitch cable PC are connected to a second plate 220 of the pitch control part 200 and to a second plate of the pitch actuating part 600, so the end effector 120, similar to the end effector in the first embodiment, operates in a pitch direction corresponding to a motion of the adjustment handle 110 in the pitch direction.

Figure 39:
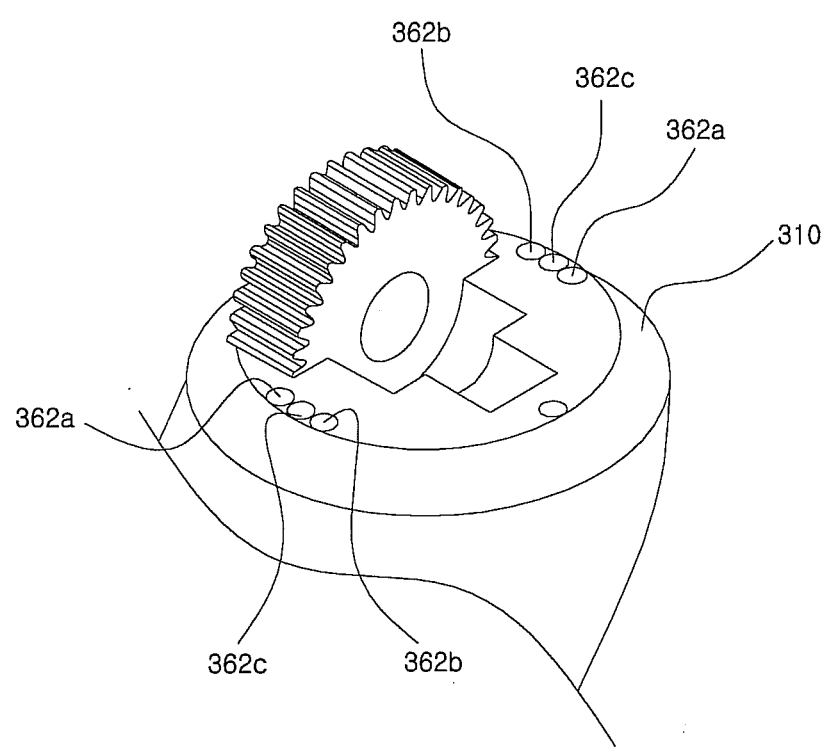
FIG. 39 shows a configuration of yaw cable insert holes in a first plate of a first yaw control part in accordance with the fourth embodiment of the present invention.

Next, as noted before, all the three yaw cables YC1, YC2 and YC3 cross the first yaw control part 300. Here, the first yaw control part 300 is configured as shown in FIG. 39. Referring to FIG. 39, among three yaw cable insert holes formed in a first plate 310 of the first yaw control part 300, the insert holes in the middle are referred to as third yaw cable insert holes 362c, and the insert holes on either side of the third yaw cable insert hole 362c are referred to as first and second cable insert holes 362a and 362b, respectively. The first, second and third yaw cable insert holes 362a, 362b and 362c are formed in symmetry or 180 degrees with respect to the central axis of the first plate 310 of the first yaw control part 300. As shown in FIG. 36, such configuration can be implemented even in the first yaw actuating part 700. Meanwhile, as shown in FIG. 37, yaw cable insert holes similar to the ones discussed above can be prepared in the second and the third yaw control parts 400 and 500, or the second and third yaw actuating parts 800 and 900 (but this configuration of yaw cable insert holes may vary depending on selective insertion of yaw cables as illustrated in FIGS. 35 to 38).

The following is an explanation on how the minimally invasive surgical tool in accordance with the fourth embodiment of the present invention with the configuration described above can be operated.

Figure 40:
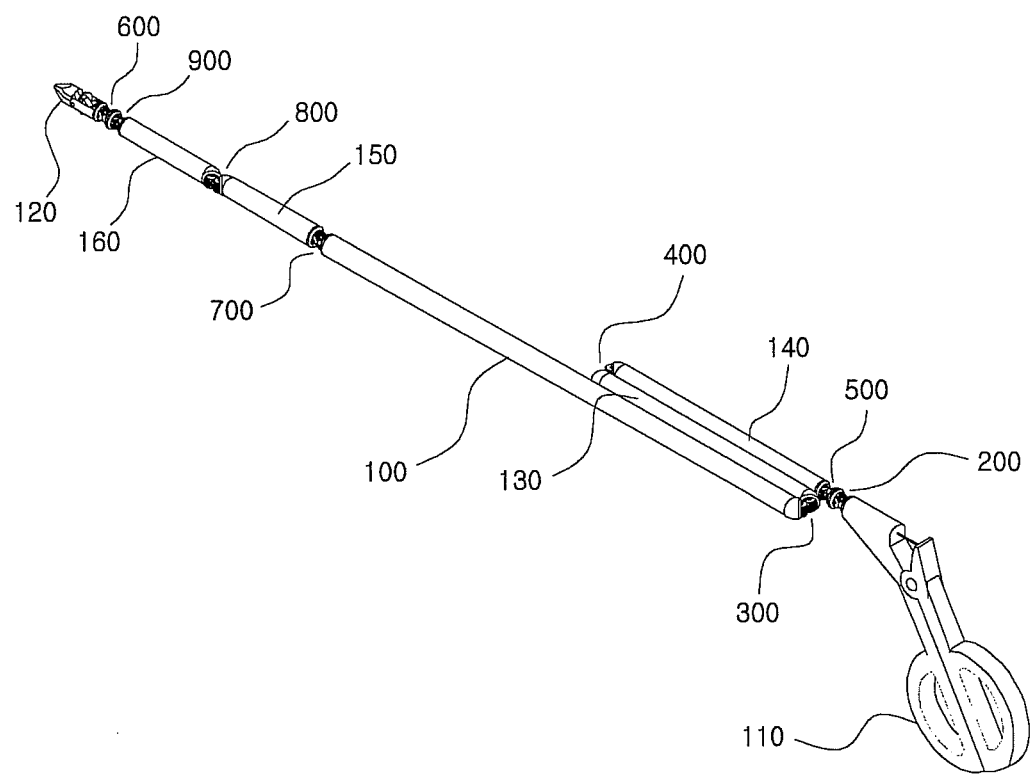
FIGS. 40, 41, and 42 show an example of a tool for minimally invasive surgery in operation in accordance with the fourth embodiment of the present invention.

First, the minimally invasive surgical tool is arranged as shown in FIG. 40.

Next, a user who performs the minimally invasive surgery puts his or her hand in the enclosure 112 of the adjustment handle 110 that is installed at one end of the tool 1 for minimally invasive surgery and holds the adjustment handle 110.

As in the previous embodiments, the end effector 120 operates in a pitch direction corresponding to a motion of the adjustment handle 110 in the pitch direction, so no further details will be provided here.

Figure 41:
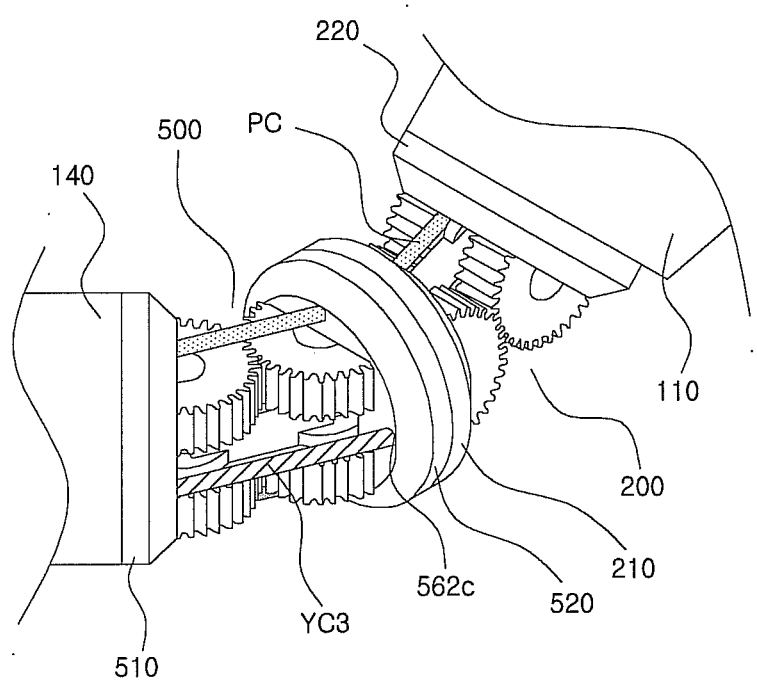

Meanwhile, when the user holding the adjustment handle 110 rotates the adjustment handle 110 to the right as shown in FIG. 41, the left yaw cable YC3 out of the third yaw cables YC3 having one end connectively secured into the third yaw cable insert holes 562c that are formed in the second plate 520 of the third yaw control part 500 in contact with the second plate 220 of the pitch control part 200 is pulled towards the user's body, so that the right side yaw cable YC3 out of the third yaw cable YC3 is released farther from the user.

Figure 42:
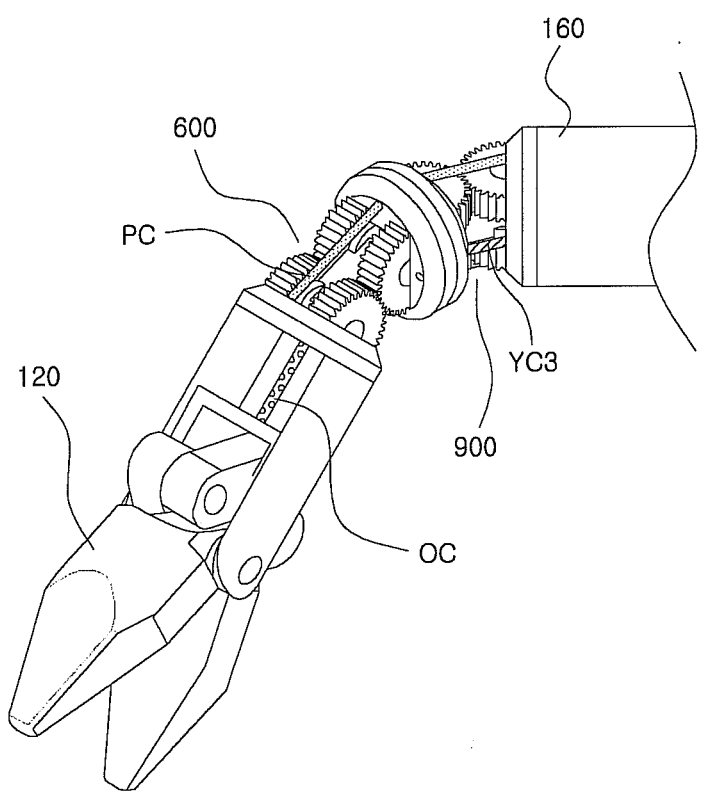

Since the other end of each of the third yaw cables YC3 is connectively secured into third yaw cable insert holes (not shown) that are formed in a second plate of the third yaw actuating part 900, the third yaw cable YC3 pulled towards the user's body causes the end effector 120 to rotate to the left, as shown in FIG. 42.

Besides, the first and the second yaw actuating parts 700 and 800 are operated by the first and the second yaw control parts 400 and 500, respectively, in exactly the same manner as those in the previous embodiments, so they will not be explained in further details.

Figure 43:
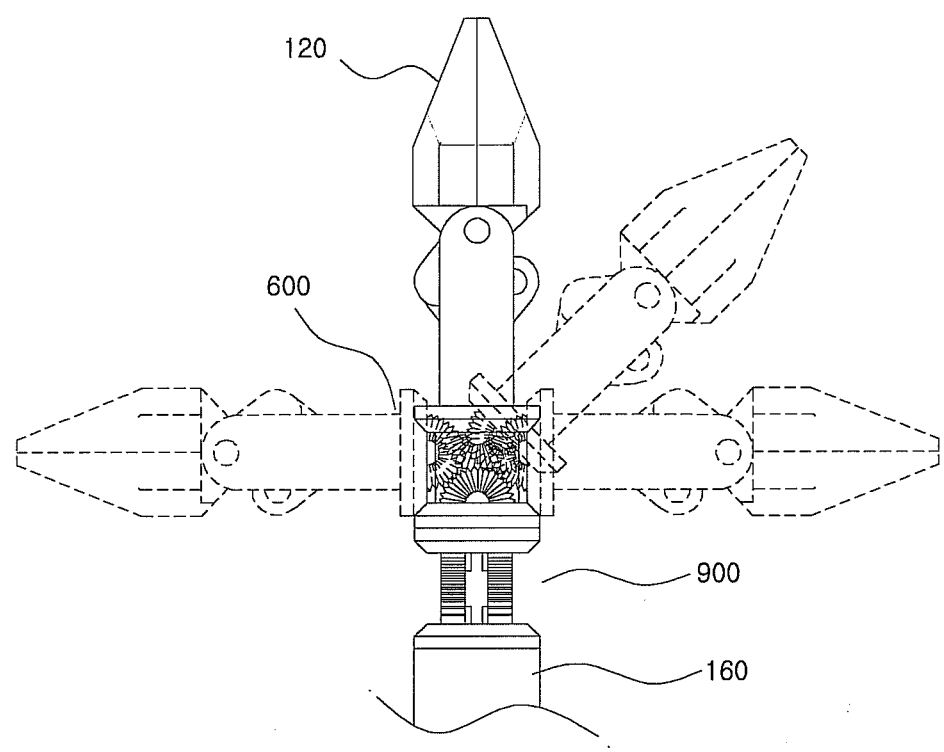
FIGS. 43 and 44 show an example of a tool for minimally invasive surgery in operation in accordance with the fourth embodiment of the present invention.
Figure 44:
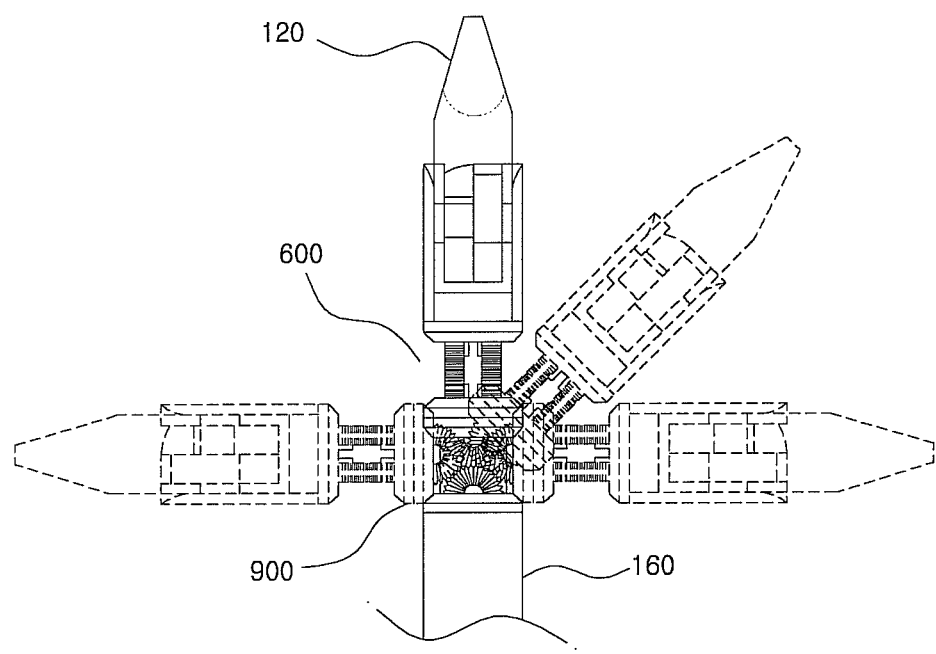

In accordance with this embodiment, the end effector 120 may be operated by the third yaw actuating part 900 as well. This means that the end effector now has more freedom in its motion, compared with the end effectors in the previous embodiments. An example of such a motion is shown in FIGS. 43 and 44.

Embodiment 5

Figure 45:
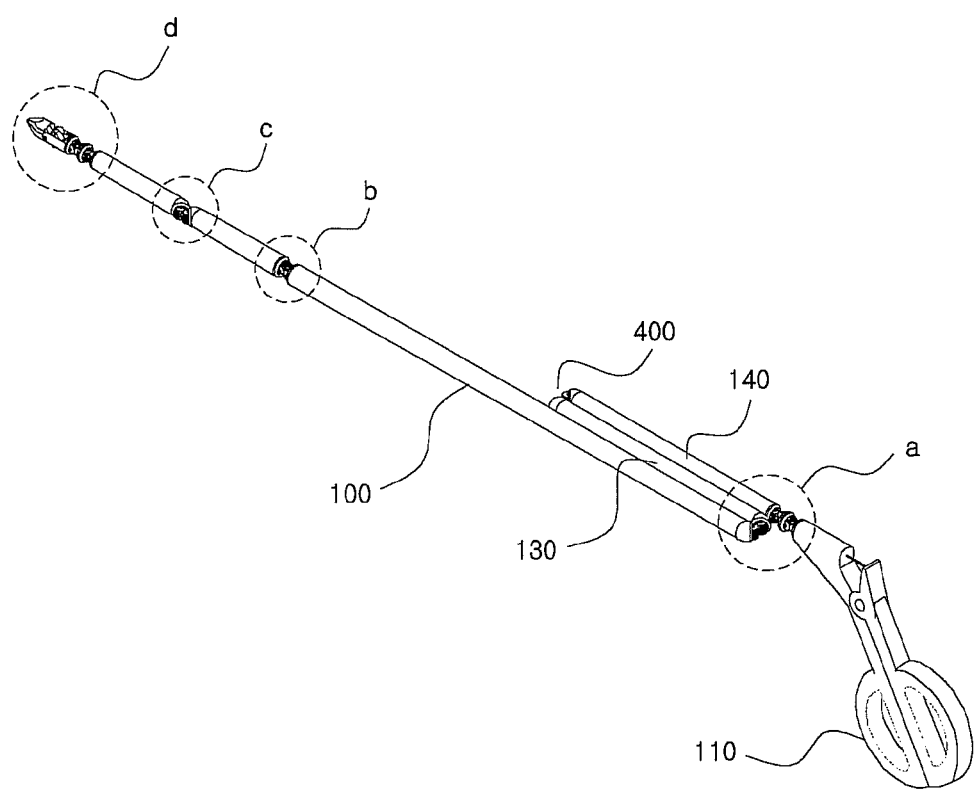
FIG. 45 is a perspective view of showing the outer appearance of a tool for minimally invasive surgery in accordance with a fifth embodiment of the present invention.
Figure 46:
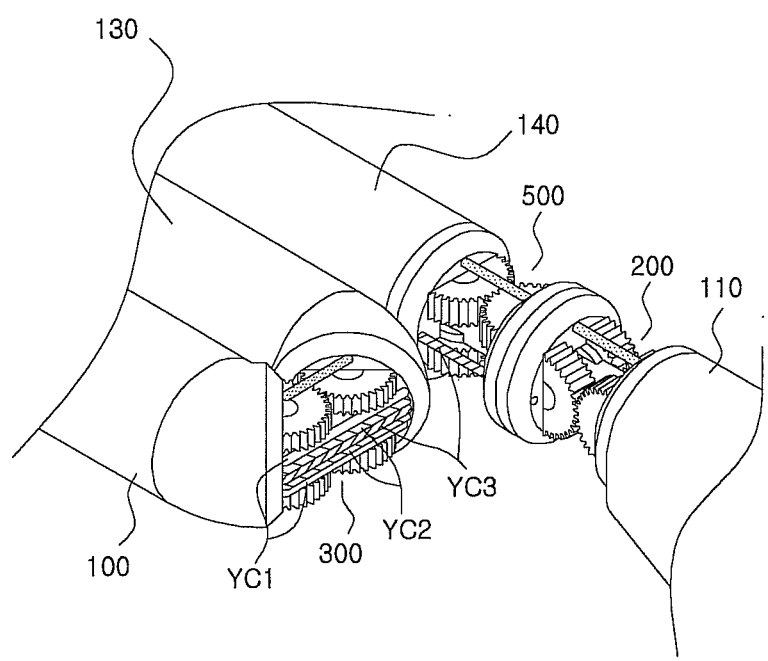
FIGS. 46 to 49 show detailed views of a, b, c and d area in FIG. 45, respectively.
Figure 47:
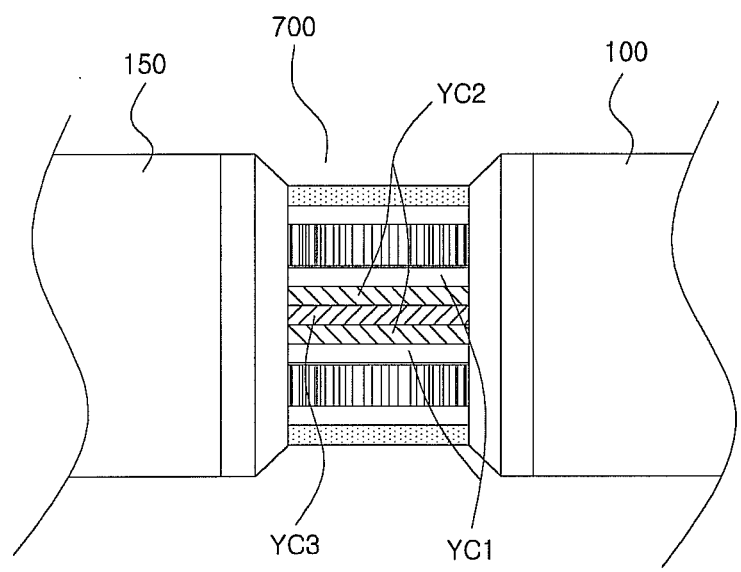
Figure 48:
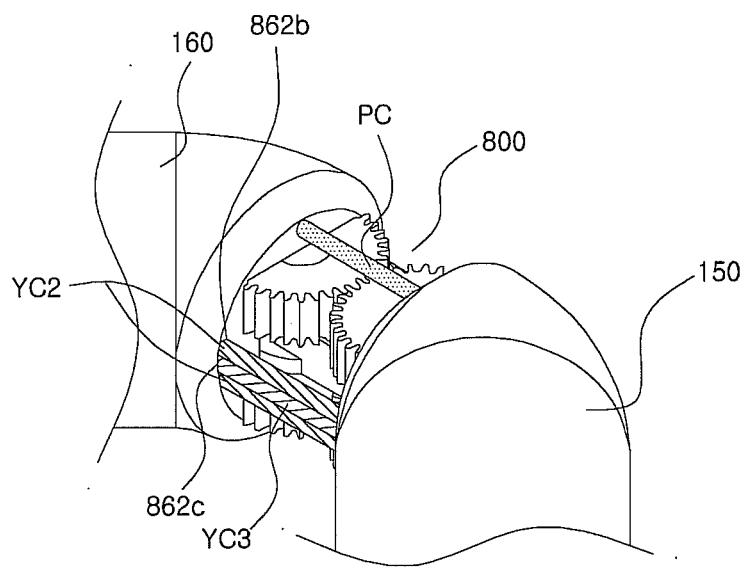
Figure 49:
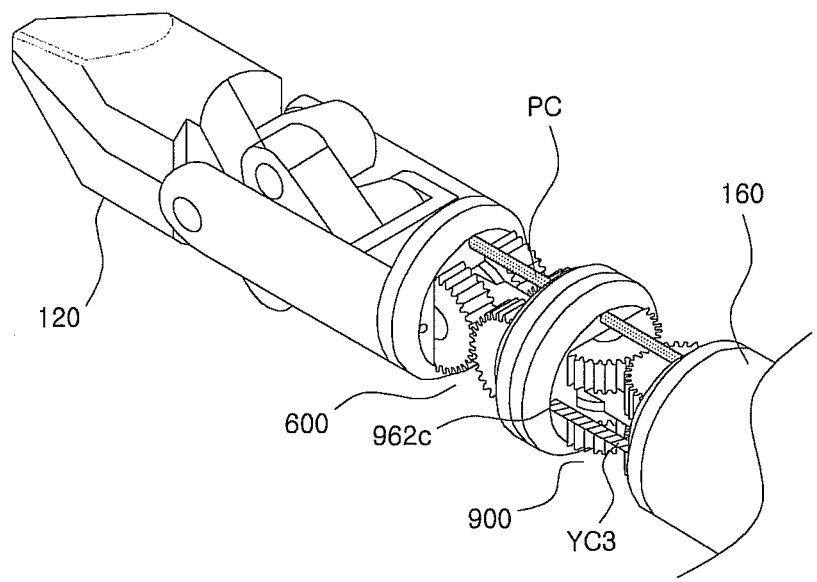

FIG. 45 is a perspective view of showing the outer appearance of a tool for minimally invasive surgery in accordance with a fifth embodiment of the present invention. In this embodiment, similar to the fourth embodiment, a third yaw control part 500 is additionally installed near a pitch control part 200 that connects an adjustment handle 110 and a second control shaft 140, and a third yaw actuating part 900 is additionally installed near a pitch actuating part 600 that connects an end effector 120 and a second actuating shaft 160.

Figure 50:
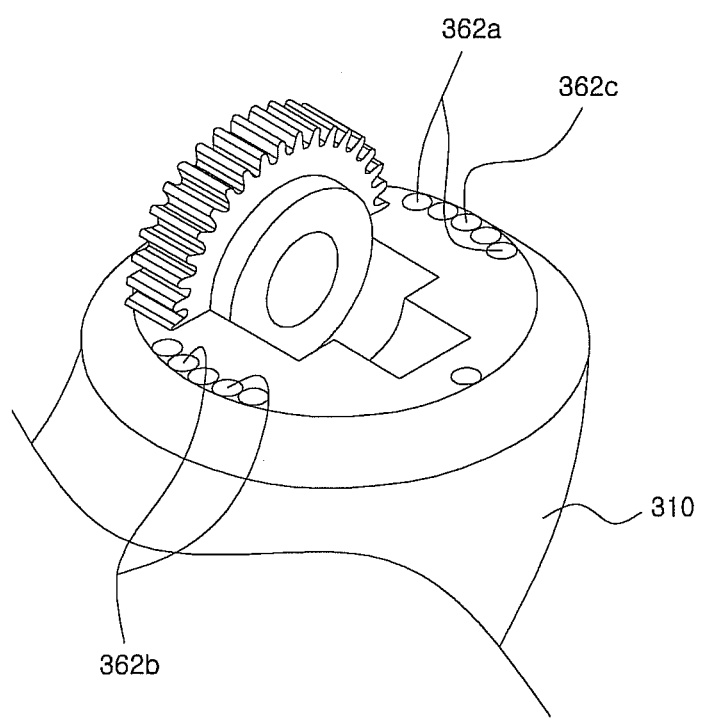
FIG. 50 shows a configuration of yaw cable insert holes in a first plate of a first yaw control part in accordance with the fifth embodiment of the present invention.

However, this embodiment differs from the fourth embodiment in that second and third yaw cables YC2 and YC3 can be disposed on either side of a first yaw cable YC1 in pairs, respectively. Such connection of yaw cables is shown in FIGS. 46, 47, 48 and 49, which are configured to correspond to FIGS. 35, 36, 37 and 38, respectively. As illustrated in FIG. 50, five yaw cable insert holes 362a, 362b and 362c may be formed in a first plate 310 of a first yaw control part 300, and five yaw cable insert holes may also be formed in a plate of a first yaw actuating part 700. In addition, plates of the second and the third yaw control parts 400 and 500 may have an equal or less (if necessary) number of yaw cable insert holes with plates of the second and the third yaw actuating parts 800 and 900.

The following is a detailed explanation about specific application examples of the present invention, which are achieved by employing at least one of the above embodiments or by adopting such application examples to at least one of the embodiments.

Application Example 1

Figure 51:
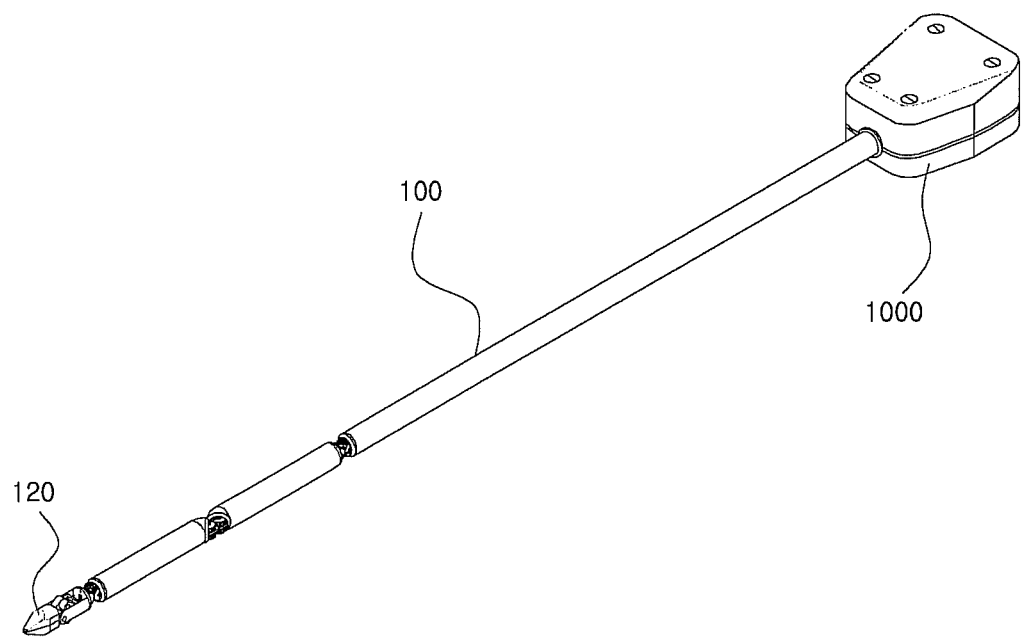
FIG. 51 is a perspective view showing the outer appearance of a tool for minimally invasive surgery in accordance with a first application example of the present invention.

FIG. 51 is a perspective view showing the outer appearance of a tool for minimally invasive surgery in accordance with the present invention, which shows that a controller 1000 performing functions of the adjustment handle 110 and the first and the second control shafts 130 and 140 in the first embodiment is connected to one end of a shaft 100.

Here, the controller 1000 can be electrically controlled by an electromotive means such as a motor to make a motion in a pitch/yaw direction as the adjustment handle 110 of the previous embodiments has done.

Any person skilled in the art can freely take a configuration for the controller 1000 by applying conventional electric drive control techniques. Some exemplary configurations for the controller 1000 can be found in related arts, U.S. Pat. No. 4,853,874 entitled "Master-slave Manipulator with Scaling", U.S. Pat. No. 5,779,623 entitled "Positioner for Medical Instruments", and U.S. Pat. No. 6,102,850 entitled "Medical Robotic System".

However, it should be understood that these specific related arts are mentioned merely for illustrative purposes, not for limiting the configuration of the controller 1000 of the present invention in any intentional way.

Application Example 2

Figure 52:
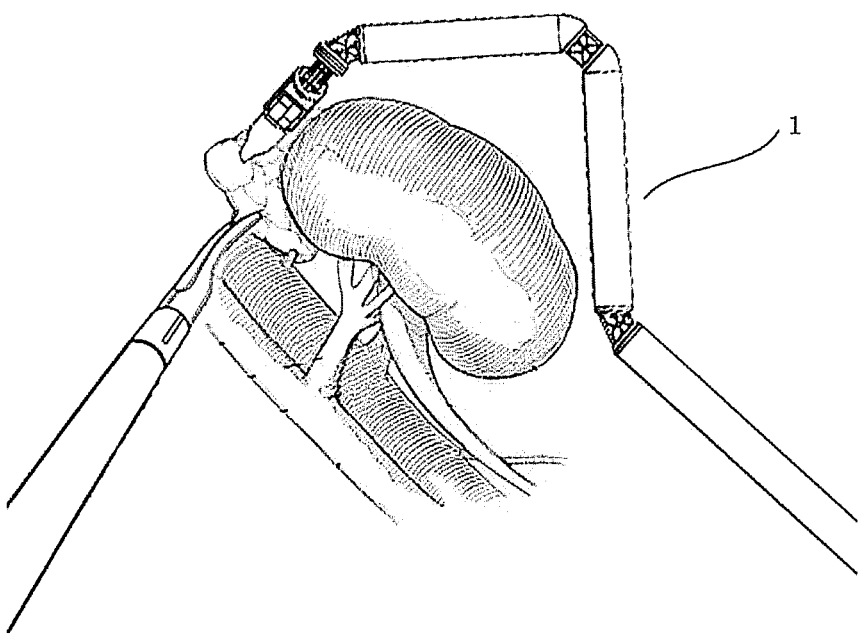
FIG. 52 is a perspective view showing the outer appearance of a tool for minimally invasive surgery in accordance with a second application example of the present invention.

Under the present invention, particularly, under the fourth embodiment or the fifth embodiment of the present invention, the degree of freedom in a yaw direction is excessively large that a surgery may be impeded by that. To resolve this, as shown in FIG. 52, a B/F nut 134 may be fastened to a bolt outside of a first control shaft 130, and a curved guide 136 having one end being secured onto a shaft 100 and the other end being bolted may be installed. By doing so, a displacement pattern of the first yaw control part 300 is properly fixed, and further a displacement pattern of a first actuating part 700 is fixed, thereby making an additional control in the yaw direction using the other yaw control parts.

In relation to this application example, it should be understood that such elements that are installed at the shaft 100 and the first control shaft 130 may also be installed at the first control shaft 130 and the second control shaft 140, and that any other elements may be employed as long as they can restrict the motion of any of the shafts.

Application Example 3

Hereinafter, examples of how to utilize the minimally invasive surgical tool of the present invention that has been taught in easy-to-understand manner through the embodiments set forth above will be introduced with reference to FIGS. 53 and 54.

Figure 53:
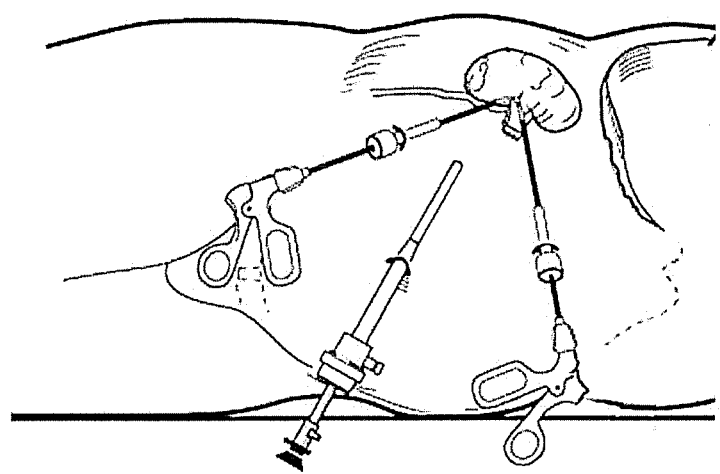
FIGS. 53 and 54 show a usage example of a tool for minimally invasive surgery in accordance with a third application example of the present invention.
Figure 54:
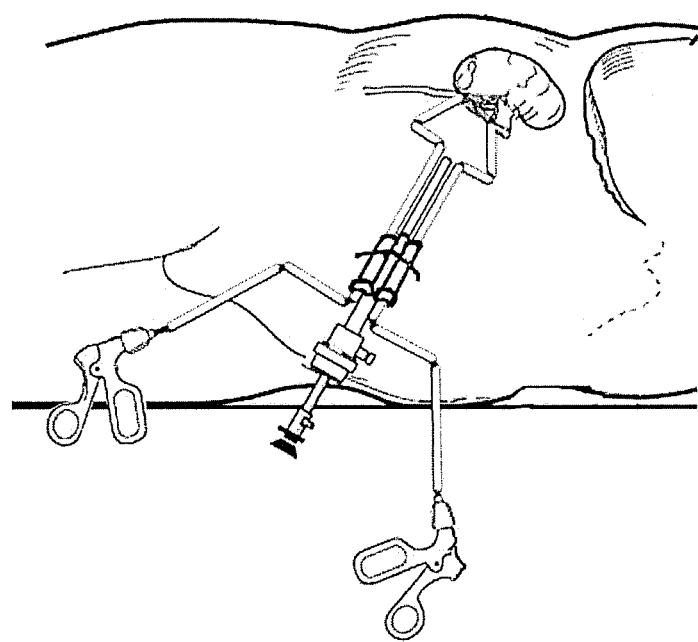

First, according to one application example of the present invention, it takes only one incision for surgery, contrarily to forming plural incisions as shown in FIG. 53 in a patient's body. FIG. 54 illustrates a case where two tools for minimally invasive surgery of the present invention are inserted in parallel through only one incision to perform a surgery. In this case, it is preferable that the two tools for minimally invasive surgery are provided to perform symmetrical motions to each other, as shown. That is, a surgeon may hold a tool in each hand and perform a surgery. Optionally, an endoscope may be additionally inserted through one incision as shown in FIG. 54 (one of benefits of this case is that a parallel arrangement between the endoscope and the surgical tool is easily secured, so the surgeon becomes aware of his or her action more intuitively).

Needless to say, the method for using the minimally invasive surgical tool in accordance with the present invention is not limited to the one discussed above. For example, an endoscope and one tool for minimally invasive surgery of the present invention may be inserted through one incision for surgery to let them stay side by side, or another tool of related art may be further inserted through one incision for surgery while the endoscope and one tool for minimally invasive surgery of the present invention have been inserted through the same incision to stay side by side.

The two minimally invasive surgical tools can be arranged in parallel and perform symmetrical motions because the plates that constitute the first and the second yaw control parts and the second yaw actuating part of the present invention are inclined, facing each other, such that one can move the tools without causing any collision between instruments.

Moreover, it is not necessary to set a limit to the number of surgical tools to be inserted through one incision, and wide variety of surgical tools can be freely used as technical advances bring lighter, smaller, and finer surgical tools.

Application Example 4

Figure 55:
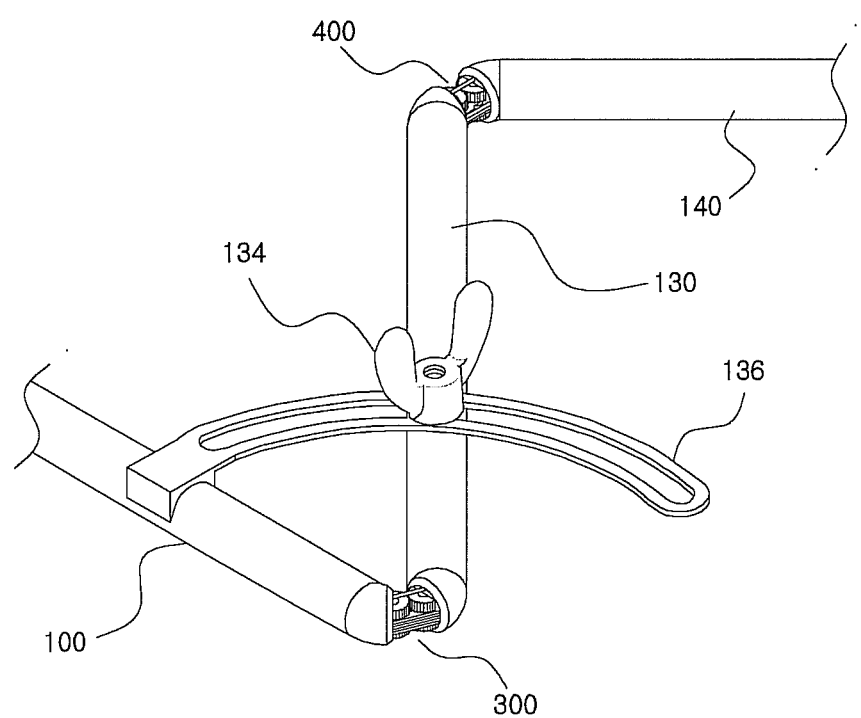
FIG. 55 shows a usage example of a tool for minimally invasive surgery in accordance with a fourth application example of the present invention.

Referring to FIG. 55, a more simple and intuitive example will be helpful to understand advantages of the present invention. FIG. 55 is an exemplary view showing that the tool of the present invention can access relatively easily to an adrenal passing by the kidney which is one of organs in a patient's body. That is, using the minimally invasive surgical tool of the present invention can make high-degree-of-freedom motion to perform a necessary surgery, by easily avoiding an organ in the way without a limitation to the position of an incision.

In accordance with the present invention having the configurations as above, the following remarkable effects can be achieved.

1. In accordance with the present invention, provided is a minimally invasive surgical tool, the end effector of which operates corresponding to the operations in pitch and yaw directions and/or the opening and closing operations from an adjustment handle.

2. In accordance with the present invention, provided is a minimally invasive surgical tool that can be freely controlled by a user without any complicated control element. Further, in accordance with the present invention, provided is a minimally invasive surgical tool that can dexterously operate with a relatively simple drive control element.

3. In accordance with the present invention, provided is a minimally invasive surgical tool that has small volume and weight and may be easily moved.

4. In accordance with the present invention, provided is a minimally invasive surgical tool, which has a plurality of joint portions so that it can access an area hidden by a specific human organ for surgery.

5. In accordance with the present invention, provided is a minimally invasive surgical tool, which requires only a minimum number of incisions (preferably, only one incision) on a patient's body for surgery and still enables an elaborate and easy surgical operation.

6. In accordance with the present invention, provided is a minimally invasive surgical tool, which is more advanced than the minimally invasive surgical tool described in Korean Patent Application Nos. 2008-51248 and No. 2008-61894 previously filed by the present inventor.

7. In accordance with the present invention, provided is a novel method to use the minimally invasive surgical tool according to the present invention.

While the present invention has been described with respect to certain preferred embodiments, it will be apparent to those skilled in the art that various changes and modifications may be made without departing from the scope of the invention as defined in the following claims.

The invention claimed is:

1. Tool for minimally invasive surgery comprising,
a main shaft,
a first control shaft and a second control shaft positioned in sequence from one end of the main shaft,
a first actuating shaft and a second actuating shaft positioned in sequence from the other end of the main shaft,
an adjustment handle positioned around one end of the second control shaft,
an end effector positioned around one end of the second actuating shaft,
a pitch control part positioned around one position of the positions between the main shaft and the first control shaft, between the first control shaft and the second control shaft, and between the second control shaft and the adjustment handle, for transferring a motion of the adjustment handle in a pitch direction to the end effector,
a first yaw control part and a second yaw control part positioned around the other positions of the positions between the main shaft and the first control shaft, between the first control shaft and the second control shaft, and between the second control shaft and the adjustment handle, respectively, for transferring a motion of the adjustment handle in a yaw direction to the end effector,
a pitch actuating part positioned around one position of the positions between the main shaft and the first actuating shaft, between the first actuating shaft and the second actuating shaft, and between the second actuating shaft and the end effector,
a first yaw actuating part and a second yaw actuating part positioned around the other positions of the positions between the main shaft and the first actuating shaft, between the first actuating shaft and the second actuating shaft, and between the second actuating shaft and the end effector, respectively, and
a pitch cable, a first yaw cable, and a second yaw cable for transferring motions from the pitch control part, the first yaw control part, and the second yaw control part to the pitch actuating part, the first yaw actuating part, and the second yaw actuating part, respectively,
wherein at least one of the pitch control part, the first yaw control part, the second yaw control part, the pitch actuating part, the first yaw actuating part, and the second yaw actuating part comprises a pair of plates, a pair of adjustment gears disposed onto each of the pair of plates, a joint rotation axis inserted in the middle between each of the pair of adjustment gears, and a link for enabling the pairs of adjustment gears on each of the pair of plates to intermesh, the link is placed between each of the pair of plates perpendicularly and between each of the pair of adjustment gears of each of the pair of plates,
wherein each of the pair of plates is spaced apart from each other by a predetermined distance and the pair of adjustment gears are disposed on perpendicular to the planes of each of the pair of plates, the pair of adjustment gears disposed on the same plane of each of the pair of plates are parallel to each other with respect to the center axis of the plate,
wherein each of the at least two adjustment gears is in semi-circular shape and includes a circular space disposed on the plane of each of the pair of plates between each of the pair of adjustment gears, the joint rotation axis is rotatably inserted in the circular space, and
wherein the pair of plates are inclined at an angle of approximately 45 degrees to an orthogonal direction to each of the corresponding shafts.

2. The tool as claimed in claim 1, wherein the adjustment handle and the end effector are configured to open and close, and further comprising an opening and closing cable for transferring the opening and closing operation of the adjustment handle to the end effector.

3. The tool as claimed in claim 2, wherein at least one space is formed inside at least one of the main shaft, the first control shaft, the second control shaft, the first actuating shaft, and the second actuating shaft.

4. The tool as claimed in claim 1, wherein at least one space is formed inside at least one of the main shaft, the first control shaft, the second control shaft, the first actuating shaft, and the second actuating shaft.

5. The tool as claimed in claim 4, wherein at least a portion of the cables are positioned through at least part of the space.

6. The tool as claimed in claim 1, wherein a plurality of cable insert holes are formed on the pair of plates.

7. The tool as claimed in claim 6, wherein the pitch cable is connected and fixed to pitch cable insert holes formed on the pitch control part or the pitch actuating part, the first yaw cable is connected and fixed to first yaw cable insert holes formed on the first yaw control part or the first yaw actuating part, and the second yaw cable is connected and fixed to second yaw cable insert holes formed on the second yaw control part or the second yaw actuating part.

8. The tool as claimed in claim 1, wherein the link comprises,
a body in a substantially cuboid shape, and
at least two rotation rings, each being formed at either end of the body and configured to enable the joint rotation axis to rotate.

9. The tool as claimed in claim 8, wherein the body has a through hole formed along its central axis of a length direction.

10. Method for using a tool for minimally invasive surgery comprising,
inserting at least one tool as claimed in claim 1 through an incision of a patient's body.

11. Method for using tools for minimally invasive surgery comprising,
inserting a first tool and a second tool as claimed in claim 1 through an incision of a patient's body, wherein a range of motion of the first tool in a yaw direction is substantially symmetrical to a range of motion of the second tool in a yaw direction.

12. Method as claimed in claim 11, wherein the first tool and the second tool are inserted in parallel.

* * * * *